（12) United States Patent
Groff

(10) Patent No.: US 12,410,393 B2
(45) Date of Patent: *Sep. 9, 2025

(54) E. COLI STRAINS HAVING AN OXIDATIVE CYTOPLASM

(71) Applicant: Sutro Biopharma, Inc., South San Francisco, CA (US)

(72) Inventor: Daniel Groff, Alameda, CA (US)

(73) Assignee: Sutro Biopharma, Inc., South San Francisco, CA (US)

( * ) Notice: Subject to any disclaimer, the term of this patent is extended or adjusted under 35 U.S.C. 154(b) by 121 days.

This patent is subject to a terminal disclaimer.

(21) Appl. No.: 17/852,907

(22) Filed: Jun. 29, 2022

(65) Prior Publication Data

US 2023/0002722 A1    Jan. 5, 2023

Related U.S. Application Data

(63) Continuation of application No. 17/282,842, filed as application No. PCT/US2019/060345 on Nov. 7, 2019, now Pat. No. 11,407,975.

(60) Provisional application No. 62/757,498, filed on Nov. 8, 2018.

(51) Int. Cl.
| C12N 1/20 | (2006.01) |
| C07K 14/47 | (2006.01) |
| C07K 16/00 | (2006.01) |
| C07K 16/32 | (2006.01) |
| C12N 9/00 | (2006.01) |
| C12N 9/02 | (2006.01) |
| C12N 9/12 | (2006.01) |
| C12N 9/90 | (2006.01) |
| C12N 15/52 | (2006.01) |
| C12N 15/70 | (2006.01) |
| C12P 21/02 | (2006.01) |

(52) U.S. Cl.
CPC .............. *C12N 1/205* (2021.05); *C07K 16/32* (2013.01); *C12N 9/0051* (2013.01); *C12N 9/1252* (2013.01); *C12N 9/90* (2013.01); *C12N 9/93* (2013.01); *C12N 15/52* (2013.01); *C12N 15/70* (2013.01); *C12Y 108/01009* (2013.01); *C12Y 207/07007* (2013.01); *C12Y 503/04001* (2013.01); *C12Y 603/02002* (2013.01); *C07K 2317/14* (2013.01)

(58) Field of Classification Search
CPC ... C12N 1/20; C12N 9/90; C12N 9/02; C12N 15/52; C12N 9/12; C12N 15/70; C12N 9/00; C07K 16/32

See application file for complete search history.

(56) References Cited

U.S. PATENT DOCUMENTS

| 4,816,397 A | 3/1989 | Boss et al. |
| 8,288,148 B2 | 10/2012 | Cervin et al. |
| 8,574,869 B2 | 11/2013 | Kao et al. |
| 8,685,668 B2 | 4/2014 | Minea et al. |
| 8,802,394 B2 | 8/2014 | Minea et al. |
| 8,852,886 B2 | 10/2014 | Dubois et al. |
| 8,877,916 B2 | 11/2014 | Alexandrov et al. |
| 9,416,388 B2 | 8/2016 | Ruddock et al. |
| 9,976,164 B2 | 5/2018 | Ruddock |
| 10,093,704 B2 | 10/2018 | Oganesyan et al. |
| 10,465,197 B2 | 11/2019 | McClain et al. |
| 2006/0030022 A1* | 2/2006 | Beckwith ............. C12N 9/0004 435/471 |
| 2019/0112357 A1 | 4/2019 | Ahuja et al. |
| 2020/0172915 A1 | 6/2020 | McClain et al. |

FOREIGN PATENT DOCUMENTS

| EP | 2298880 | * 3/2011 |
| EP | 3360960 A1 | 8/2018 |
| WO | 2009/118651 A1 | 10/2009 |
| WO | 2011/100362 A1 | 8/2011 |
| WO | 2013/185115 A1 | 12/2013 |
| WO | 2017/093254 A1 | 6/2017 |

OTHER PUBLICATIONS

Stewart et al., The Embo Journal, 17, 5543-5550, Nov. 1998.*
Gaciarz, et al., "Systematic Screening of Soluble Expression of Antibody Fragments in the Cytoplasm of *E. coli*", Microbial Cell Factories, vol. 15, No. 22, pp. 1-10 (2016).
PCT/US2019/060345 , "International Preliminary Report on Patentability", May 20, 2021, 7 pages.
Robinson, "Remodeling Antibodies from the Inside Out: Functional Engineering of Full-Length Antibodies in the Cytoplasm of Bacteria," Ph.D. Dissertation, Cornell University, 149 pages (Dec. 2017).
Gaciarz, et al., "Efficient soluble expression of disulfide bonded proteins in the cytoplasm of *Escherichia coli* in fed-batch fermentations on chemically defined minimal media", Microbial Cell Factories, vol. 16, No. 108, 12 pages (2017).
Kaur, et al., "Strategies for Optimization of Heterologous Protein Expression in *E. coli*: Roadblocks and Reinforcements", International Journal of Biological Macromolecules, vol. 106, pp. 803-822 (2018).
Lobstein, et al., "SHuffle, A Novel *Escherichia coli* Protein Expression Strain Capable of Correctly Folding Disulfide Bonded Proteins in its Cytoplasm", Microbial Cell Factories, vol. 11, No. 1, 16 pages (2012).

(Continued)

Primary Examiner — Maryam Monshipouri
(74) Attorney, Agent, or Firm — Kilpatrick Townsend and Stockton LLP

(57) ABSTRACT

This disclosure provides an *E. coli* strain, which lacks thioredoxin reductase activity encoded by trxB and thioredoxin 1 activity encoded by trxA, and glutathione reductase activity encoded by gor. Said *E. coli* strain expresses a mutated AhpC protein having glutathione reductase activity and a cytosolic prokaryotic disulfide isomerase. The *E. coli* strain has an oxidative cytosol and can be used to efficiently produce proteins having disulfide bonds.

23 Claims, 4 Drawing Sheets

Specification includes a Sequence Listing.

(56) References Cited

OTHER PUBLICATIONS

Monje-Casas, et al., JBC, 276(21), pp. 18031-18037 (Feb. 2001).
Robinson, et al., "Efficient Expression of Full-Length Antibodies in the Cytoplasm of Engineered Bacteria", Nature Communications, vol. 6, 9 pages (Aug. 27, 2015).
PCT/US2019/060345, "International Search Report and Written Opinion", Mar. 24, 2020, 10 pages.
Lee, et al., "Enhanced production of human full length immunoglobulin G1 in the periplasm of Escherichia coli.," Applied Microbiology and Biotechnology. Springer Berlin Heidlburg vol. 98, No. 3, Nov. 26, 2013) (2013).
Axup, et al., "Synthesis of site specific antibody-drug conjugates using unnatural amino acids," Proceedings to the National Academy of Sciences vol. 109, No. 40, Oct. 2, 12, 2012. (2012).
Li, et al., Sutro Biopharma, Poster AACR, 2018. (2018).
Nowroozi, et al., Metabolic pathway optimization using ribosome binding site variants and combinatorial gene assembly. Appl. Microbiol. Biotechnol, vol. 98, pp. 1567-1581. (2014).
Vo, et al., Optimized expression of Hfq protein increases Escherichia coli growth by enhancing acid resistance, Authorea, vol. 2, pp. 1-14. (2020).
Kessler, et al., "Expression, purification, and isotope labeling of the Fv of the human H IV-1 neutralizing antibody 447-52D for NM R studies.," Prot. Express. Purification., vol. 29: 291-303. (2003).
Gleiter, et al., "Disulfide bond isomerization in prokaryotes", Biochim Biophys Acta, 1783(4), pp. 530-534, Feb. 23, 2008.

\* cited by examiner

E. COLI STRAINS HAVING AN OXIDATIVE CYTOPLASM

RELATED APPLICATION

This application is a continuation of U.S. application Ser. No. 17/282,842, filed Apr. 5, 2021, which is a U.S. National Phase under 35 U.S.C. § 371 of Application No. PCT/US2019/060345, filed Nov. 7, 2019, which claims priority to U.S. Provisional Application No. 62/757,498, filed Nov. 8, 2018. The disclosures of which are incorporated herein by reference in their entireties for all purposes.

REFERENCE TO SEQUENCE LISTING

This application includes a Sequence Listing as a text file named "091200-1327572-006720US_SEQ_LIST.txt" created Jun. 28, 2022, and containing 27,935 bytes. The material contained in this text file is incorporated by reference in its entirety for all purposes.

BACKGROUND OF THE INVENTION

Commercially valuable proteins, such as therapeutic proteins, often possess disulfide bonds. These disulfide bonds are important for protein stability and function. Conventional bacterial hosts for protein production have a reductive cytosol and thus are unable to form disulfide bonds in proteins expressed in the cytosol. As a result, currently many proteins cannot readily be expressed in bacterial cytosol and are instead expressed in eukaryotic or periplasmic expression systems. Although attempts to promote disulfide bond formation in bacterial cytosol have been made by introducing mutations into the bacterial host genome to disrupt reductive pathways, these efforts have yielded limited success. Thus, cytosolic production of disulfide-bonded proteins in bacteria remains a challenge.

SUMMARY OF INVENTION

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

In some embodiments, the disclosure provides an E. coli strain, which lacks thioredoxin reductase activity encoded by trxB and thioredoxin 1 activity encoded by trxA, and glutathione reductase activity encoded by gor. Said E. coli strain expresses a mutated AhpC protein having glutathione reductase activity and a cytosolic prokaryotic disulfide isomerase. In some embodiments, the mutated AhpC protein is AhpC*. In some embodiments, the E. coli strain expresses both a wild type AhpC protein and a mutated AhpC protein having glutathione reductase activity.

In some embodiments, the strain further comprises a gene encoding a protein of interest. The protein of interest may be one selected from the group consisting of: an antibody, a fragment thereof or an antibody+light chain from an IgG. In some embodiments, the E. coli further expresses a recombinant prolyl isomerase.

In some embodiments, the cytosolic disulfide isomerase expressed in the E. coli is a DsbC.

In some embodiments, the gene encoding the protein of interest is operably linked to an inducible promoter, e.g., a T7 promoter. In some embodiments, the T7 promoter can be induced by arabinose. In some embodiments, the expression of the ahpC* gene in the E. coli is controlled by a Pc0 promoter. In some embodiments, the expression of the cytosolic prokaryotic disulfide isomerase in the E. coli is controlled by an MTL promoter. In some embodiments, the E. coli is from a K-12 strain.

Also provided herein is a method for expressing soluble, recombinant proteins of interest in E. coli bacterial strains comprising the steps of: culturing an E. coli bacterial strain comprising an oxidizing cytosol and an expression cassette for expressing a protein of interest under conditions that permit expression of the protein of interest as a soluble protein, wherein the strain is genetically modified as follows: i) the thioredoxin reductase encoding gene, trxB is not functional; ii) the thioredoxin 1 trxA is not functional; iii) the glutathione reductase gene (gor) is not functional; iv) an ahpC gene that has been mutated such that expressed enzyme lacks peroxyreductase activity and has glutathione reductase activity; and v) a gene encoding a cytosolic prokaryotic disulfide isomerase has been recombinantly introduced into the bacterial strain. In some embodiments, the E. coli strain comprises a functional gene ahpC gene and a mutated ahpC gene. In some embodiments, the mutated ahpC gene is ahpC*. In some embodiments, the trxC gene is non-functional. In some embodiments, the trx B gene is non-functional.

In some embodiments, the cytosolic disulfide isomerase is DsbC or yeast protein disulfide isomerase (yPDI). In some embodiments, the E. coli strain further expresses one or more recombinant prolyl isomerase. In some embodiments, the recombinant prolyl isomerase is selected from the group consisting of, cyclophilin, FKBPs, parvulin, SlyD, Tig, and yCpr6. In some embodiments, the E. coli strain further expresses one or more deaggregases. In some embodiments the deaggregase is selected from the group consisting of Skp, GroEL, GroES, DnaK, DnaJ, and GrpE.

In some embodiments, the E. coli expresses a protein of interest that is selected from the group consisting of: an IgG, a light chain from an IgG or a heavy chain from an IgG. In some embodiments, the antibody light chain is a light chain of an anti-HER2 antibody. In some embodiments, the gene encoding the protein of interest is operably linked to an inducible promoter, e.g., a T7 promoter. In some embodiments, the E. coli strain further express a T7 polymerase. In some embodiments, the T7 polymerase is under the control of an inducible promoter. In some embodiments, the inducible prompter is a $P_{araBAD}$, lac, phoA, tetA, xylAB, tac, or rhamnose promoter. In some embodiments, the T7 polymerase may recognize T7 promoter, which controls the expression of the protein of interest.

In some embodiments, the E. coli strain expresses GshA encoded by the gshA gene. In some embodiments, the gshA is a recombinant gene that is inserted into the locus of TrxB.

Also provided herein is a kit comprising the E. coli of any of the embodiments above, and the kit further comprises a growth medium. The kit may further comprise a plasmid encoding a protein of interest.

BRIEF DESCRIPTION TO THE DRAWINGS

DETAILED DESCRIPTION OF THE INVENTION

Introduction

Figure 1A:
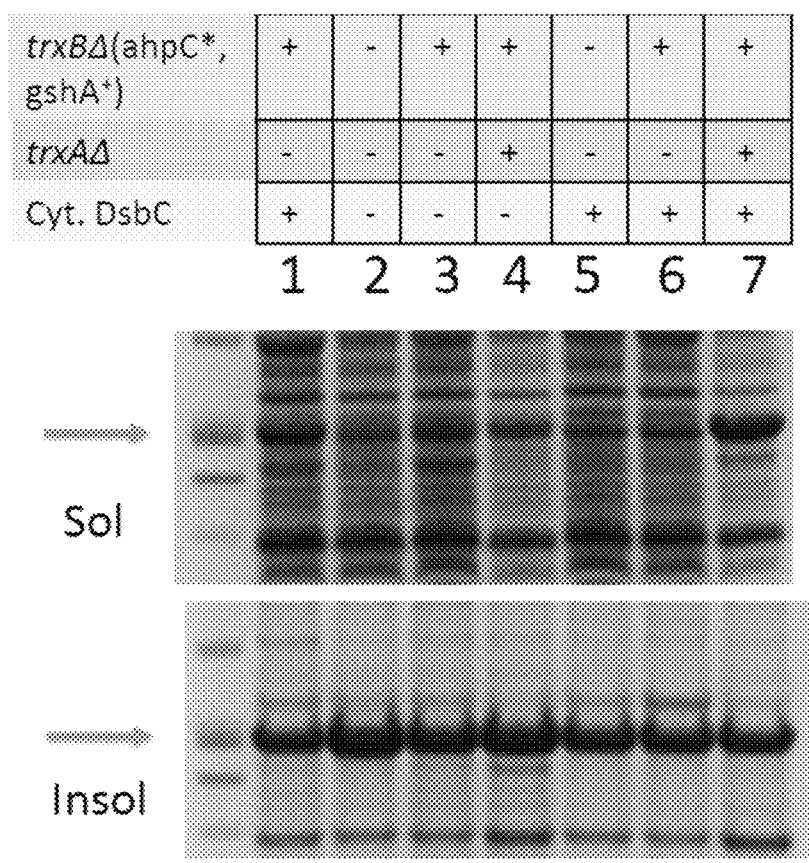
FIG. 1A shows the results of SDS PAGE analysis of the soluble and insoluble fractions of cell lysates from seven modified E. coli strains expressing the antibody light chain (LC) of an anti-Muc1 antibody, Muc1 G09k LC. The various mutations in these *E. coli* strains are shown in the table above the SDS-PAGE results.

This disclosure provides an *E. coli* strain that has been genetically engineered to contain an oxidative cytoplasm. Such oxidative cytoplasm is essential for maintaining the three-dimensional structure and stability of proteins having disulfide bonds. The invention provides a production system based on *E. coli* to produce a protein such as an antibody light chain (LC) with high yield.

Previously, a mutant *E. coli* strain ("Shuffle") was generated. Lobstein et al., Microbial Cell Factories 2012, 11:56. This mutant strain lacks the thioredoxin reductase activity (TRXB) and glutathione reductase activity (GOR). The Shuffle also overexpresses a DsbC without its signal sequence and a variant of the ahpC gene (ahpC*) encoding an enzyme that lacks perioxireductase activity but has glutathione reductase activity. Shuffle was reported to show ability to produce correctly folded disulfide bonded proteins.

As compared to Shuffle, the *E. coli* strain disclosed herein have been further engineered so that it further lacks the thioredoxin 1 activity (TrxA). Thus, in some embodiments, the *E. coli* strain comprises null mutations in trxA, trxB, and gor. Consequently, the strain lacks the thioredoxin reductase activity (TrxB), thioredoxin 1 activity (TrxA), and glutathione reductase activity (GOR). The *E. coli* strain disclosed herein also overexpresses a DsbC without its signal sequence and overexpresses a variant of the ahpC gene (ahpC*) that encoded an enzyme that lacks perioxireductase activity but has glutathione reductase activity.

Surprisingly, the *E. coli* strain disclosed herein can produce a higher yield of some disulfide-bonded proteins as compared to Shuffle. Given that trxB encodes the cytoplasmic thioredoxin reductase that reversibly reduces an oxidized thioredoxin encoded by trxA; according to conventional thinking, inactivating thioredoxin reductase should have rendered inactivation of the substrate, thioredoxin 1, unnecessary, since the former is upstream of the latter in the redox biochemical pathway. It thus is a surprise that the *E. coli* strain lacking both TrxA and TrxB provides a superior yield of some soluble biologically active proteins containing disulfide bonds.

Definition

The term "reductase" refers to a thioredoxin reductase (TrxB), glutathione or glutathione reductase (Gor) or any other enzyme that can reduce members of the thioredoxin or glutaredoxin systems.

The term "thioredoxin" includes thioredoxin 1 (TrxA) and thioredoxin 2 (TrxC), as described in Rietsch and Beckwith (1998) Ann. Rev. Genet. 32: 163. Thioredoxins are small proteins characterized by the presence of the motif Cys-Xaa-Xaa-Cys (where Xaa denotes any amino acid) in their active site. Thioredoxin is re-reduced by thioredoxin reductase (encoded by the trxB gene) and NADPH. In a trxB mutant, thioredoxin accumulates in an oxidized form. TrxA is encoded by the trxA gene and TrxB is encoded by the trxB gene.

The term "gor" refers to the glutathione oxidoreductase gene and the term "GOR" refers to glutathione oxidoreductase.

"DsbC", is a protein encoded by the gene dsbC, which catalyzes disulfide bond isomerization. DsbC null mutants have a defect in the folding of proteins with multiple disulfide bonds.

The term "glutathione" refers to γ-L-glutamyl-L-cysteinyl-glycine (GSH), which is a highly conserved low molecular weight thiol found in many organisms including cyanobacteria, proteobacteria, a few strains of gram-positive bacteria, and in all eukaryotes having mitochondria and chloroplasts. Glutathione is synthesized by the action of two enzymes: glutamate-cysteine ligase (gshA) and glutathione synthetase (gshB). Glutamate-cysteine ligase catalyzes the reaction between glutamic acid and cysteine to form γ-glutamyl cysteine, which is subsequently conjugated to glycine by glutathione synthetase to form GSH.

A nucleic acid is "operably linked" to another nucleic acid when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, the synthetic oligonucleotide adaptors or linkers are used in accordance with conventional practice.

AhpC is one of the two subunits of the alkyl hydrogen peroxide reductase AhpCF. The other subunit of AhpCF is flavoenzyme AhpF. Tarataglia et al, J. Biol. Chem., Volume 265, 10535-10540, 1990; Smillie et al, Genbank submission NCBL gi; 216542, 1993). These two proteins act together; AhpF uses NADH or NADPH as electron donor to AhpC, which reduces physiological lipid peroxides such as linoleic acid hydroperoxide and thymine hydroperoxide and non-physiological alkyl hydroperoxides to their respective non-toxic alcohol forms. This enzymatic complex (or system) scavenges oxygen and its derivatives. AhpC has been demonstrated to act as specific alkyl hydroperoxide-scavenging enzyme for protection against oxygen radical damage, though elimination of reactive nitrogen intermediates also has been demonstrated to occur. AhpF is related to thioredoxin reductases possessing an extended additional N-terminal fragment essential to specifically reduce AhpC.

The term "cytosolic" when used to describe a protein refers to that the protein is present in the cytosol of the cell.

A "heterologous protein or polypeptide" refers to a protein or polypeptide which is not normally produced in the host cell. A heterologous polypeptide can be from the same species and type as the host cell provided that it is expressed from a nucleic acid which has been introduced into the host cell.

An "exogenous polypeptide" refers to a polypeptide that is not normally produced in the cell.

A "null mutation" refers to a mutation in a gene that result in a nonfunctional gene. The null mutation can cause complete lack of production of associated gene product or a product that does not function properly.

The term "protein disulfide isomerase," used interchangeably with the term "disulfide isomerase," or "PDI," refers to an enzyme that catalyzes disulfide bond formation and isomerization. PDI has been implicated in the catalysis of disulfide bond formation and rearrangement through in vitro data. (Creighton et al. (1980) *J. Mol. Biol.* 142:43; Feedman et al. (1989) *Biochem. Soc. Symp.* 5:167; and Bardwell and Beckwith (1993) *Cell* 74:899. Yeast mutants in PDI have been shown to have a defect in the formation of disulfide bonds in carboxypeptidase Y (LaMantia and Lennarz (1993) *Cell* 74:899). Use of PDI for expression of heterologous proteins in host cells is further described in PCI application having publication No. WO 93/25676; WO 94/08012; and EP 509,841.

The term "prolyl isomerase," used interchangeably with "peptidylprolyl isomerase" or "PPlase", refers to an enzyme found in both prokaryotes and eukaryotes that interconverts the cis and trans isomers of peptide bonds with the amino acid proline. Proteins with prolyl isomerase activity include, but are not limited to, cyclophilin (e.g., accession #Q13427), FKBPs (e.g., accession #Q02790), parvulin (e.g., accession #Q9Y237), Tig (e.g., accession #P0A850), SlyD (e.g., accession #P0A9K9), and yCpr6 (e.g., accession #S000004206).

The term "deaggregase" refers to a protein chaperone that aids in deaggregating and/or solubilizing proteins of interest that are produced, for example, in a bacterial free translation system. Such chaperones are particularly helpful at high concentrations because their mechanism of action is stoichiometric rather than catalytic and is believed to work by stabilizing hydrophobic patches of the newly synthesized protein while the protein is folding. Non-limiting examples of deaggregases include Skp (e.g., accession #P0AEU7), GroEL (e.g., accession #P0A6F5), GroES (e.g., accession #P0A6F9), DnaK (e.g., accession #P0A6Y8), DnaJ (e.g., accession #P08622), GrpE (e.g., accession #P09372), or.

When referring to a protein in a "reduced state," it refers to the protein having more electrons than its oxidized form.

The term "oxidative cytoplasm" refers to the cytosol of a cell in which a substrate is more likely to become oxidized than reduced.

The term "thioredoxin reductase activity" refers to the ability of thioredoxin reductase (TRXB) to maintain thioredoxin 1 in the reduced state.

The term "thioredoxin 1 activity" refers to the ability of thioredoxin) (TRXA) to maintain ribonucleotide reductase at reduced state.

The term "peroxyreductase activity" refers to the ability of AhpC to reduce physiological lipid oxide.

The term "glutathione reductase activity" refers to the ability of catalyzing the reduction of glutathione disulfide (GSSG) to the sulfhydryl form glutathione (GSH). For example, glutathione reductase (GOR) possesses the glutathione reductase activity.

The term "recombinant" or "recombinantly", refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

Modifying Reducing Pathways in *E. coli*.

The invention alters two reductive pathways in *E. coli* to produce properly folded cytoplasmic protein with disulfide bonds: the thioredoxin pathway and the glutaredoxin/glutathione pathway.

In the thioredoxin pathway, thioredoxin reductase (the product of the trxB gene) uses the reducing potential of NADPH to maintain thioredoxin 1 (the product of the trxA gene) in a reduced state, so that thioredoxin 1 in turn can reduce substrate proteins such as ribonucleotide reductase. This pathway can be eliminated as long as there is a glutathione or glutaredoxin pathway present in the cell. This was accomplished in the current invention through the chromosomal deletion of trxA and trxB.

In the glutathione/glutaredoxin pathway, glutathione oxidoreductase (the product of the gor gene) uses the reducing potential of NADPH to reduce glutathione (encoded by gshA and gshB). Glutathione is then able to reduce three glutaredoxins (encoded by grxA, grxB, and grxC). Stewart et al., EMBO J. Vol. 17 No. 19 pp. 5543-5550 (1998). In the current invention, this pathway was modified so that glutathione is reduced via a mutated peroxyreductase rather than GOR.

The *E. coli* strain disclosed herein has been genetically modified such that it has different reductive pathways as compared to the wild type *E. coli*. In some embodiments, the *E. coli* stain contains a mutated ahpC gene that encodes a mutated AhpC protein. In some embodiments, the mutated AphC protein gains the activity of a glutathione reductase and therefore can restore the growth of a trxB gor mutant *E. coli* strain. In preferred embodiments, the mutated AphC protein retains the cysteine residue at position 165 as compared to the wild type AphC protein. These mutants can channel electrons into the glutathione/glutaredoxin pathway, rather than the thioredoxin pathway. In some embodiments, the mutated AphC protein lacks the peroxyreductase activity that the wild type AhpC protein possesses. In some embodiments, the mutated AphC protein retains the peroxyreductase activity that the wild type AhpC protein possesses.

In some embodiments, the mutated AphC protein contains one or more point mutations relative to the wild type AphC and the one or more point mutations do not involve the cysteine residue at position 165. In some embodiments, one or more point mutations are selected from the group consisting of S159P, P161S, A167T, P166S, C46Y, C46F, R119C, and G141S. In some embodiments, these mutant AhpC proteins retain the peroxyreductase activity that the wild type AhpC possesses. Some of these mutants are described in Yamamoto et al., Mol. Cell. January 18; 29(1): 36-45 (2008), the relevant disclosure is herein incorporated by reference.

In some embodiments, the mutated aphC gene is SEQ ID NO: 4 (hereinafter the "ahpC* gene"), which encodes SEQ ID NO: 5 (hereinafter the "AhpC* protein). The AhpC* protein loses the peroxyreductase activity the wild type AhpC protein possesses, but gains the activity of a glutathione reductase. The AhpC* contains an insertion of a phenylalanine between residue 36 and 37 of the wild type AhpC protein. In some embodiments, the ahpC* gene is inserted into the scar site left by the FLP recombinase from deletion of that gene. In one example, the ahpC* is inserted into the scar site in the tnaA (tryptophanase) locus from deletion of that gene.

The *E. coli* strain has also been genetically engineered such that it lacks thioredoxin reductase activity. In one embodiment, the *E. coli* contains a null mutation in the trxB gene, which results in the bacteria lacking the thioredoxin reductase activity.

The *E. coli* strain has also been genetically engineered such that it lacks the thioredoxin 1 activity. In one embodiment, the *E. coli* contains a null mutation in the trxA gene, which results in the bacteria lacking the thioredoxin reductase activity.

The *E. coli* strain has also been genetically engineered such that the glutathione reductase gene (gor), is not functional. In one embodiment, the *E. coli* contains a null mutation in the gor gene, which results in the bacteria lacking the glutathione reductase activity.

In some embodiments, the *E. coli* strain expresses a gshA gene. GshA is responsible for the first step of glutathione biosynthesis, and expressing a function GshA protein can ensure the cell still possess a functional glutathione synthesis pathway and ensure cell survival.

The *E. coli* strain has also been modified to express a recombinant cytosolic prokaryotic disulfide isomerase. The recombinant cytosolic prokaryotic disulfide isomerase can facilitate protein folding, which is especially important for more challenging LCs. In some embodiments, the chaperone is localized to cytoplasm by removal of the leader sequence for secretion out of the cell. In one embodiment, the disulfide isomerase is DsbC. In one embodiment, the disulfide isomerase is yeast protein disulfide isomerase (yPDI), e.g., as described in Groff et al., MAbs 6(3): 671-678 (2014), which shows that yPDI and DsbC were functionally interchangeable for the folding of immunoglobulin proteins in prokaryotic systems. It is thus expected that human protein disulfide isomerase and other closely related proteins are also suitable for functional replacement of DsbC in this strain. In some embodiments, the protein isomerase is a prolyl isomerase, and suitable prolyl isomerase may be include, but are not limited to, cyclophilin, FKBPs, parvulin, deaggregase skP or slyD, groEL/groES, danK, dnaJ, or grpE.

The signal sequence that must be removed to convert a secreted chaperone into a cytosolic chaperone can be identified in multiple ways. For well-characterized organisms such as *E. coli* and humans, the signal sequences are known for most proteins. This reduces the task of eliminating the secretion sequence to simply removing this sequence during cloning. For less studied organisms including other bacteria or animals, the signal sequence can still be inferred through homology to their bacterial or human homologs. In cases in which there are no homologs with known signal sequences, there are algorithms for predicting signal sequences which are correct around 70% of the time, Nielsen H, Engelbrecht J, Brunak S, and von Heijne G. Protein Eng. 1997 January; 10(1):1-6.

Protein of Interest

The methods provided herein can be used for any protein having at least one disulfide bond in its biologically active confirmation or which, in the mature form does not contain a disulfide bond, but a precursor of which contains at least one disulfide bond.

Disulfide bonds are typically formed by the oxidation of sulfhydryl groups between two cysteine side chains resulting in a covalent bond. Disulfide bonds can stabilize tertiary protein structure by locking folding units into stable conformations by linking residues in a covalent manner. Many of the disulfide-bonded proteins are secreted or remain anchored to the plasma membrane, exposed to the environment. These features of the disulfide-bonded proteins make them excellent therapeutic agents or targets for the pharmaceutical industry.

In prokaryotic cells, disulfide bonds are formed when DsbA protein donates its disulfide bond to a newly synthesized polypeptide that comprises a disulfide bond in its native structure. The integral membrane protein DsbB generates disulfide bonds within itself, which are then transferred to DsbA. DsbC is a protein that catalyzes disulfide bond isomerization. In wild type *E. coli* strain, DsbC is exported to the periplasm and is thus unsuitable for production of cytoplasmic, disulfide-containing proteins. As disclosed herein, in some embodiments, the modified *E. coli* strain expresses a cytosolic prokaryotic disulfide isomerase, e.g., DsbC. This cytosolic DsbC protein is expressed without its signal sequence; as a result this DsbC protein remains in the cytoplasm to promote disulfide assembly of proteins of interest. In some eukaryotic cells, the major disulfide pathway is composed of the membrane-associated flavoprotein EroI and the soluble thioredoxin-like protein PDI. EroI, using a flavin cofactor to mediate the reoxidation of its cysteine pair by oxygen, generates disulfide bonds within itself, and then transfers the bonds to PDI. In turn, PDI transfers the disulfide bonds directly to newly synthesized polypeptides that have not adopted their native structure.

Disulfide bonds are present in numerous proteins including, but not limited to secreted proteins, immune proteins, extracellular matrix proteins, glycoproteins, lysosomal proteins and membrane proteins. Detailed descriptions of disulfide bonds and proteins with disulfide bonds can be found in, e.g., Fass, D. *Annu. Rev. Biophys.*, 2012, 41:63-79, Sevier, C. S. and Kaiser, C. A. *Antioxidants & Redox Signaling*, 2006, 8(5):797-811 and de Marco, A., *Microbial Cell Factories*, 2009, 8:26. These proteins can also be produced using the system disclosed herein.

The protein of interest can be eukaryotic, prokaryotic proteins, viral proteins, or plant proteins. In some embodiments, the protein of interest is of mammalian origin, including murine, bovine, ovine, feline, porcine, canine, goat, equine, and primate origin. In some embodiments, the protein of interest is of human origin.

In some embodiments, the protein of interest is an antibody, such as single chain antibodies, a fragment of an antibody, as well as antibodies consisting of multiple polypeptide chains. In some embodiments, the protein of interest is a light chain or heavy chain of an antibody. In some embodiments, the protein of interest is an scFv. In some embodiments, the protein of interest is a Fab fragment. Exemplary antibodies include but are not limited to anti-HER2 antibody. An exemplary light chain includes, but is not limited to, a light chain of an anti-HER2 antibody, e.g., a trastuzumab light chain.

Additional examples of proteins of interest which can be produced include the following proteins: mammalian polypeptides including molecules such as, e.g., renin, growth hormone, receptors for hormones or growth factors; CD proteins such as CD-3, CD4, CD8, and CD-19; interleukins; interferons; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

A protein produced by the invention can be used for one or more of the following purposes or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, the ability to bind antigens or complement); and the ability to act as an antigen in vaccine composition to raise an immune response against such protein or another material or entity which is cross-reactive with such protein.

The polypeptides and proteins produced by the invention can be used for any purpose known to one of skill in the art. Preferred uses include medical uses, including diagnostic uses, prophylactic and therapeutic uses. For example, the proteins can be prepared for topical or other type of administration. Another preferred medical use is for the preparation of vaccines. Accordingly, the proteins produced by the invention are solubilized or suspended in pharmacologically acceptable solutions to form pharmaceutical compositions for administration to a subject. Appropriate buffers for medical purposes and methods of administration of the pharmaceutical compositions are further set forth below. It will be understood by a person of skill in the art that medical compositions can also be administered to subjects other than humans, such as for veterinary purposes.

General Methods

Unless defined otherwise, all technical and scientific terms used herein have the meaning commonly understood by one of ordinary skill in the art to which this invention belongs. Practitioners are particularly directed to Green, M. R., and Sambrook, J., eds., Molecular Cloning: A Laboratory Manual, 4th ed., Cold Spring Harbor Laboratory Press, Cold Spring Harbor, N.Y. (2012), and Ausubel, F. M., et al., Current Protocols in Molecular Biology (Supplement 99), John Wiley & Sons, New York (2012), which are incorporated herein by reference, for definitions and terms of the art. Standard methods also appear in Bindereif, Schón, & Westhof (2005) Handbook of RNA Biochemistry, Wiley-VCH, Weinheim, Germany which describes detailed methods for RNA manipulation and analysis, and is incorporated herein by reference. Examples of appropriate molecular techniques for generating recombinant nucleic acids, and instructions sufficient to direct persons of skill through many cloning exercises are found in Green, M. R., and Sambrook, J., (Id.); Ausubel, F. M., et al., (Id.); Berger and Kimmel, Guide to Molecular Cloning Techniques, Methods in Enzymology (Volume 152 Academic Press, Inc., San Diego, Calif. 1987); and PCR Protocols: A Guide to Methods and Applications (Academic Press, San Diego, Calif. 1990), which are incorporated by reference herein.

Methods for protein purification, chromatography, electrophoresis, centrifugation, and crystallization are described in Coligan et al. (2000) Current Protocols in Protein Science, Vol. 1, John Wiley and Sons, Inc., New York. Methods for cell-free synthesis are described in Spirin & Swartz (2008) Cell-free Protein Synthesis, Wiley-VCH, Weinheim, Germany. Methods for incorporation of non-native amino acids into proteins using cell-free synthesis are described in Shimizu et al (2006) FEBS Journal, 273, 4133-4140.

PCR amplification methods are well known in the art and are described, for example, in Innis et al., PCR Protocols: A Guide to Methods and Applications, Academic Press Inc. San Diego, Calif., 1990. An amplification reaction typically includes the DNA that is to be amplified, a thermostable DNA polymerase, two oligonucleotide primers, deoxynucleotide triphosphates (dNTPs), reaction buffer and magnesium. Typically a desirable number of thermal cycles is between 1 and 25. Methods for primer design and optimization of PCR conditions are well known in the art and can be found in standard molecular biology texts such as Ausubel et al., Short Protocols in Molecular Biology, $5^{th}$ Edition, Wiley, 2002, and Innis et al., PCR Protocols, Academic Press, 1990. Computer programs are useful in the design of primers with the required specificity and optimal amplification properties (e.g., Oligo Version 5.0 (National Biosciences)). In some embodiments, the PCR primers may additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers may also contain an RNA polymerase promoter site, such as T7 or SP6, to allow for subsequent in vitro transcription. Methods for in vitro transcription are well known to those of skill in the art (see, e.g., Van Gelder et al., Proc. Natl. Acad. Sci. U.S.A. 87:1663-1667, 1990; Eberwine et al., Proc. Natl. Acad. Sci. U.S.A. 89:3010-3014, 1992).

When the proteins described herein are referred to by name, it is understood that this includes proteins with similar functions and similar amino acid sequences. Thus, the proteins described herein include the wild-type prototype protein, as well as homologs, polymorphic variations and recombinantly created muteins. For example, the name "DsbC protein" includes the wild-type prototype protein from *E. coli* (e.g., SEQ ID NO:1), as well as homologs from other species, polymorphic variations and recombinantly created muteins. Proteins such as DsbC are defined as having similar functions if they have substantially the same biological activity or functional capacity as the wild-type protein (e.g., at least 80% of either). Proteins such as DsbC and AhpC* are defined as having similar amino acid sequences if they have at least 80%, 85%, 90%, 95%, 96%, 97%, 98%, or 99% sequence identity to the prototype protein. The sequence identity of a protein is determined using the BLASTP program with the defaults wordlength of 3, an expectation (E) of 10, and the BLOSUM62 scoring matrix (see Henikoff and Henikoff, *Proc. Natl. Acad. Sci. USA* 89:10915-10919, 1992).

A readily conventional test to determine if a protein homolog, polymorphic variant, or a recombinant mutein is inclusive of a protein having the function described herein is by specific binding to polyclonal antibodies generated against the prototype protein. Typically a specific or selective reaction will be at least twice background signal or noise and more typically more than 10 to 100 times background.

For example, a DsbC protein includes proteins that bind to polyclonal antibodies generated against the prototype protein of SEQ ID NO:1.

Methods of Introducing Mutations to E. coli

In some embodiments, the gene modifications, e.g., the knock-outs of trxA and trxB, can be performed with a site-specific recombination. Site-specific recombination uses enzymes possessing both endonuclease activity and ligase activity and the enzymes recognize a certain part of DNA sequences and replace it with any other corresponding DNA sequences, see Yang W. and Mizuuchi K., Structure, 1997, Vol. 5, 1401-1406(9). Site-specific recombination systems are well known in the art, e.g., Int/att system from bacterio λ phage, Cre/LoxP system from PI bacteriophage and FLP-FRT system from yeast are well developed site-specific recombination systems.

Non-limiting examples of methods of introducing site specific recombination to various proteins disclosed herein include the Cre/Lox and Flp/Frt recombination systems. Both systems are well known in the art. For instance, site-specific integration into bacterial chromosomes has been reported (see, e.g., Sauer et al., Proc. Natl. Acad. Sci. 85. 5166-5170 (1988); Fukushige et al., Proc. Natl. Acad. Sci., 89. 7905-7907 (1992); Baubonis et al., Nucleic Acids Research. 21, 2025-2029 (1993); Hasan et al., Gene, 150. 51-56 (1994); Golic et al., Cell. 5_9, 499-509 (1989); Sauer, Mol. Cell. Biolo. 1, 2087-2096 (1987); Sauer et al., Methods: Companion to Methods in Enzymol. 4, 143-149 (1992); Sauer et al., The New Biologist. 2, 441-449 (1990); Sauer et al., Nucleic Acids Res. 17. 147-161 (1989); Qin et al., Proc. Natl. Acad. Sci. 91. 1706-1710 (1994); Orban et al., Proc. Natl. Acad. Sci., 89, 6861-6865 (1992)). Specific deletions of chromosomal sequences and rearrangements have also been engineered, and excision of foreign DNA as a plasmid from λ vectors is presently possible (see, e.g., Barinaga, Science. 265, 27-28 (1994); Sauer, Methods in Enzvmol. 225. 890-900 (1993); Sauer et al., Gene, 70. 331-341 (1988); Brunelli et al., Yeast, 1309-1318 (1993); Invitrogen (San Diego, Calif.) 1995 Catalog, 35; Clontech (Palo Alto, Calif.) 1995/1996 Catalog, 187-188). Cloning schemes have been generated so that recombination either reconstitutes or inactivates a functional transcription unit by either deletion or inversion of sequences between recombination sites (see, e.g., Odell et al., Plant Physiol. 106. 447-458 (1994); Gu et al., Cell. 73. 1155-1164 (1993); Lakso et al., Proc. Natl. Acad. Sci. 89. 6232-6236 (1992); Fiering et al., Proc. Natl. Acad. Sci. 90. 8469-8473 (1973); O'Gorman et al., Science. 251, 1351-55 (1991); Jung et al., Science, 259, 984-987 (1993)).

Genes encoding the Cre or Flp recombinases can be provided in trans under the control of either constitutive, inducible or developmentally-regulated promoters, or purified recombinase has been introduced (see, e.g., Baubonis et al., supra; Dang et al., Develop. Genet. 13, 367-375 (1992); Chou et al., Genetics. 131. 643-653 (1992); Morris et al., Nucleic Acids Res. 19. 5895-5900 (1991)).

In some embodiments, the genomic manipulations disclosed herein are performed with a modified site-specific recombination protocol from Kirill A. Datsenko and Barry L. Wanner Proc Natl Acad Sci USA. 2000 Jun. 6; 97(12): 6640-6645. In one embodiment, knocking out a gene for example, trxA, can be performed as follows. A PCR amplicon was generated comprising an antibiotic resistance gene flanked by two FRT sites and homology extensions, (H1 and H2), which are homologous to the two ends of the gene to be knocked out. After transforming cells with this PCR product, the gene to be knocked out is then replaced by the antibiotic resistance gene through Red-mediated recombination in these flanking homology regions. After selection, the resistance gene can be eliminated using a helper plasmid expressing the FLP recombinase, which acts on the directly repeated FRT (FLP recognition target) sites flanking the resistance gene. The Red and FLP helper plasmid can be simply cured by growth at 37° C. because they are temperature-sensitive replicons. Knocking-in a gene, such as dsbC, can be performed by standard molecular cloning techniques that are well known for one skilled in the art.

In some embodiments, the knocking out a gene] is performed using CRISPR/Cas system. The CRISPR/Cas system uses aa Cas protein and at least one to two ribonucleic acids that are capable of directing the Cas protein to a sequence in a target gene, e.g., gor, to remove the gene. Methods of using CRISPR/Cas system to eliminate gene expression are well known and described in e.g., US. Pat. Pub. No. 2014/0170753, the disclosure of which hereby is incorporated by reference in its entirety.

Additional methods of knocking out a target gene include, but are not limited to, homologous recombination technology, transcription activation of the effector nuclease (Transcription Activator-Like Effector Nuclease, TALEN) technology, a zinc finger nuclease (Zinc-Finger Nuclease, ZFN). These methods are also well known in the art.

Vectors and Promoters

A nucleic acid encoding a protein of interest, a chaperone (e.g., DsbC), or other proteins (e.g., AhpC*) can be inserted into a replicable vector for expression in the E. coli under the control of a suitable prokaryotic promoter. Many vectors are available for this purpose and one of skilled in the art can readily determine the selection of appropriate vector. Besides the gene of interest, a vector typically comprises one or more of the following: a signal sequence, an origin of replication, one or more maker genes and a promoter.

Promoters can be used may be any appropriate promoter sequence suitable for a eukaryotic or prokaryotic host cell, which shows transcriptional activity, including mutant, truncated, and hybrid promoters, and may be obtained from polynucleotides encoding extracellular or intracellular polypeptides either endogenous (native) or heterologous (foreign) to the cell. The promoter may be a constitutive or inducible promoter.

In some embodiments, the promoter is a constitutive promoter. Suitable prokaryotic promoters useful for practice of this invention include, but not limited to, the promoters of Pc0, PL59, MTL, ParaBAD, lac, T3, T7, lambda Pr'P1', trp, the spc ribosomal protein operon promotor $P_{spc}$, the β-lactamase gene promotor $P_{bla}$ of plasmid pBR322, the $P_L$ promoter of phage λ, the replication control promoters $P_{RNAI}$ and $P_{RNAII}$ of plasmid pBR322, the P1 and P2 promoters of the rrnB ribosomal RNA operon, the tet promoter, and the pACYC promoter. Tetracycline-regulated transcriptional modulators and CMV promoters are described in WO 96/01313, U.S. Pat. Nos. 5,168,062 and 5,385,839, the entire disclosures of which are incorporated herein by reference.

In some embodiments, the promoters may have different strength in terms of the amount of expression it can produce. Promoters can be a medium strength promoter, weak strength promoter and strong promoter. The strength of a promoter can be measured as the amount of transcription of a gene product initiated at that promoter, relative to a suitable control. For constitutive promoters directing expression of a gene product in an expression construct, a suitable control could use the same expression construct, except that the 'wild-type' version of the promoter, or a promoter from a 'housekeeping' gene, is used in place of the promoter to be tested.

In some embodiments, the promoter strength is determined by measuring the amount of transcripts from the promoter as compared to a control promoter. For example, host cells containing an expression construct with the promoter to be tested ('test host cells") and control host cells containing a control expression construct, can be grown in culture in replicates. The total RNA of the host cells and controls can be extracted and measured by absorbance at 260 nm. cDNA can then be synthesized from the equal amount of total RNA from the test host cells and the control host cells. RT-PCR can be performed to amplify the cDNA corresponding to the transcript produced from the promoter. An exemplary method is described in De Mey et al. ("Promoter knock-in: a novel rational method for the fine tuning of genes", BMC Biotechnol 2010 Mar. 24; 10:26).

In some embodiments, the various transgenes are expressed in the E. coli under the control of promoters of different strength to ensure the recombinant proteins, e.g., the AhpC* protein and the DsbC protein, are expressed at appropriate levels. This is useful for maintaining an oxidative cytoplasm in the bacteria and establishing an alternative reduction pathway to ensure survival, vigor (growth rate). In one embodiment, the ahpC* gene is controlled by a Pc0 promoter, a medium strength promoter. Both the PL59 promoter (a weak promoter) and a WT gshA promoter (an intermediate strength promoter) can be used to direct the expression of gshA gene. In some embodiments, a strong promoter T7 is used to drive the expression of the protein of interest to ensure maximal yield. In some embodiments, the E coli strain expresses a recombinant T7 polymerase under the control of the paraBAD promoter, which allows tight regulation and control of the protein of interest, e.g., through the addition or absence of arabinose. Guzman et al., J. Bacteriol. July 1995 177 (14): 4121-4130.

Optionally, clones of the E. coli carrying the desired modifications as disclosed herein can be selected by limited dilution. Optionally, these clones can be sequenced to confirm that the desired mutations are present in various genes, or desired transgenes, e.g., dsbC and ahpC*, are inserted into the genome. In some cases, whole genome sequencing can be performed to determine the location of the insertion or mutation in the chromosomes.

Host Cells

The E. coli strain in this disclosure can be any E. coli strain known to one of skill in the art. In some embodiments, the E. coli strain is a A (K-12), B, C or D strain.

Measuring Enzymatic Activities

In some embodiments, a mutation introduced in one or more of the genes, e.g., trxA, does not abolish protein expression or mRNA expression, but results in a mutein that lacks the activity that the corresponding wild type protein possesses, e.g., thioredoxin activity of TrxA. It is understood by one of skill in the art that sometimes knocking out a gene does not require completely abolishing its activity, thus for purpose of this disclosure, lacking an activity means the mutein loses 85-100% of the activity of the control protein, e.g., the wild type protein. The various muteins generated can be tested to confirm that they lack the activity of the wild type protein. For example, each of the coding sequences for the muteins can be separately expressed in a host strain, and the muteins are purified and tested for their activities as described below.

Confirming the Loss of Thioredoxin Reductase Activity,

In one embodiment, the thioredoxin reductase activity can be measured by its activity in reducing 5,5-Dithiobis(2-nitrobenzoic acid) (DTNB) in the presence of NADPH. The reaction is typically started by mixing DTNB with thioredoxin reductase (TrxR), thioredoxin (Trx), and NADPH, and monitoring increase in absorbance at 412 nm over time. The activity can be defined as the rate of absorbance increase. An embodiment of detecting thioredoxin reductase activity is disclosed in U.S. Pat. No. 8,592,468.

Confirming the Loss of Thioredoxin Activity

Methods for determining thioredoxin activity are also well known. In one embodiment, the assay is an insulin precipitation assay, such as described by Sung-Jong Jeon et al., European Journal of Biochemistry, Vol. 269, No. 22. Thioredoxins are known to possess an activity as disulfide reductases of insulin; and reduction of insulin disulfide bonds can be measured by the increase in turbidity due to precipitation of the free insulin B-chain. In one illustrative example; a standard assay mixture contains 0.1M potassium phosphate (pH 7.0), 1 mM EDTA, and 0.13 mM bovine insulin in the absence or in the presence of the recombinant protein, and the reaction was initiated upon the addition of 1 mM dithiothreitol. An increase of the absorbance at 650 nm was monitored at 30° C.

Confirming the Loss of Glutathione Reductase Activity

The glutathione reductase activity of the AhpC* or the loss of the glutathione reductase activity of the mutein GOR can also be monitored. In some embodiments, the glutathione reductase activity is measured by its activity in reducing cysteine. For example, cysteine were incubated with reduction solution containing the candidate protein, e.g., AhpC* or the mutein GOR, in the presence of cofactors. Preferably the cofactor is a coenzyme. Preferably the cofactor is nicotinamide adenine dinucleotide phosphate (NADPH) or nicotinamide adenine dinucleotide (NADH). The reaction reduces cystine to cysteine. The schematic reaction is as follows:

CYS–CYS+2GSH→2CYS+GSSG

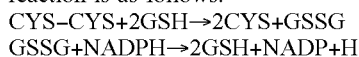

The activity can be measured by measuring the production of cysteine. In one particular example, the glutathione reductase activity in terms of reducing cysteine is described in WO2018114576.

Confirming the Loss of Peroxyreductase Activity of AhpC

The lack of peroxyreductase activity of AhpC* can be confirmed by incubating the protein with organic hydroperoxides or hydrogen peroxide in the presence of NADH. A functional peroxyreductase would convert these substrates into water in an NADH-dependent mechanism; a lack of evidence of such conversion indicates a lack of peroxyreductase activity.

Confirming the Cytosol of the E. coli Strain is at an Oxidative State

The E. coli strain disclosed herein contains an oxidative cytoplasm. This can be confirmed by the biological activity of a protein having disulfide bond for example, a LC that is difficult to express in a wild type E. coli strain. In some embodiments, confirming the E. coli have oxidative cytoplasm can be conducted by transforming the bacteria with a gene encoding a polypeptide (a "test" polypeptide) which normally contain at least one disulfide bond. Preferred test polypeptides or proteins are those which are normally secreted from cells or which are membrane proteins. In some cases, these polypeptides are modified by the deletion or mutation of the signal sequence, such that the proteins are not exported outside of the cytoplasm of the cell.

As one illustrative example, a coding sequence for the LC protein, e.g., an anti-MUC1 antibody light chain (SEQ ID NO: 15), described above can be engineered into an expression cassette under a suitable promoter and transformed into the modified *E. coli* strain. The soluble protein fraction that contain the LC is measured. A suitable *E. coli* strain will be able to express in a soluble form of at least 1 mg/100 mL of the LC. Methods for preparing a bacterial lysate and measuring the amount of protein expression (e.g., the expression of LC) in the lysate are well known. In some embodiments, the *E. coli* cells can be treated with a lysis agent to produce a lysate. Cytoplasmic proteins can be released by treating the lysate with enzymes, such as benzonase and egg white lysozyme. The insoluble protein fraction can be separated from the soluble fraction by e.g., centrifugation. The soluble protein fraction (containing the LC) can be collected and analyzed by SDS-PAGE. The amount of LC protein in the soluble protein fraction can then be quantified by e.g., densitometry. One specific example of analyzing a LC expression is described in Example 2, which can be used to assess whether the cytosol is at an oxidative state.

Confirming Expression

Various methods can be used to determine protein expression level of the various modified genes in the *E. coli*, and/or confirm whether a gene has been knocked out or inserted. For example, expression of a gene can be determined by conventional Northern blotting to quantitate the transcription of mRNA. Various labels may be employed, most commonly radioisotopes. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

In some embodiments, the expressed protein can be purified and quantified using gel electrophoresis (e.g., PAGE), Western analysis or capillary electrophoresis (e.g., Caliper LabChip). Protein synthesis in cell-free translation reactions may be monitored by the incorporation of radiolabeled amino acids, typically, $^{35}$S-labeled methionine or $^{14}$C-labeled leucine. Radiolabeled proteins can be visualized for molecular size and quantitated by autoradiography after electrophoresis or isolated by immunoprecipitation. The incorporation of recombinant His tags affords another means of purification by $Ni^{2+}$ affinity column chromatography. Protein production from expression systems can be measured as soluble protein yield or by using an assay of enzymatic or binding activity.

In some embodiments, if the protein to be quantified possesses defined biological activity, for example, enzymatic activity (such as alkaline phosphatase) or growth inhibition activity, the expression of the protein of interest can be confirmed by assaying its activity by incubating with proper substrates.

Kits of the Invention

This disclosure also provides kits that comprise a host cell of the invention and optionally a growth media, a plasmid encoding a protein of interest, a probe, an antibody, and/or instructions for use. In some embodiments, the kit may further comprise one or more necessary components for producing a biologically active or properly folded disulfide containing protein.

In some embodiments, the kit may comprise one or more reagents necessary for preparation a host cell of the invention. Such a kit may comprise one or more reagents necessary for reducing the expression of reductases or agents necessary for introducing mutations into one or more reductases of a host cell. A kit may comprise agents necessary for improving the growth of host cells, e.g., reducing agents, or a gene optionally contained in a plasmid, encoding a protein which improves growth.

Exemplary Embodiments

This disclosure includes the following non-limiting embodiments:

1. An *E. coli* strain, wherein:
i) the strain lacks thioredoxin reductase activity encoded by trxB;
ii) the strain lacks thioredoxin 1 activity encoded by trxA;
iii) the strain lacks glutathione reductase activity encoded by gor;
iv) the strain expresses a mutated AhpC protein, wherein the mutated AhpC protein has glutathione reductase activity; and,
v) the strain expresses a cytosolic prokaryotic disulfide isomerase.

2. The *E. coli* strain of embodiment 1 wherein the strain further comprises a gene encoding a protein of interest.

3. The *E. coli* strain of embodiment 2 wherein the protein of interest is selected from the group consisting of: an antibody, a fragment thereof or an antibody+light chain from an IgG.

4. The *E. coli* strain of any of the embodiments 1-3 wherein the cytosolic disulfide isomerase is DsbC.

5. The *E. coli* strain of any of the embodiments 1-4 wherein the *E. coli* further expresses a recombinant prolyl isomerase and/or a deaggregase.

6. The *E. coli* strain of any of the embodiments 1-4 wherein the prolyl isomerase is selected from the group consisting of cyclophilin, FKBPs, parvulin, SlyD, Tig, yCpr6;
and wherein the deaggregase is selected from the group consisting of Skp, GroEL, GroES, DnaK, DnaJ, and GrpE.

7. The *E. coli* strain of any of the embodiments 2-6 wherein the gene encoding the protein of interest is operably linked to a constitutive promoter.

8. The *E. coli* strain of any of the embodiments 2-7 wherein the gene encoding the protein of interest is operably linked to a T7 promoter.

9. The *E. coli* strain of any of the embodiments 1-8, wherein the expression of the mutated ahpC gene is controlled by a Pc0 promoter.

10. The *E. coli* strain of any of the embodiments 1-9, wherein the expression of the cytosolic prokaryotic disulfide isomerase is controlled by a MTL promoter.

11. The *E. coli* strain of any of embodiments 1-9, wherein the *E. coli* strain is a K-12 strain.

12. A method for expressing soluble, recombinant proteins of interest in *E. coli* bacterial strains comprising the steps of:
a. culturing an *E. coli* bacterial strain comprising an oxidizing cytosol and an expression cassette for expressing a protein of interest under conditions that permit expression of the protein of interest as a soluble protein, wherein: the strain is derived from a wild type bacterial strain having a functional thioredoxin reductase encoding gene, trxB; a functional thioredoxin 1 encoding gene, trxA, a functional thioredoxin 2 encoding gene trxC; a functional glutathione reductase gene (gor) and a functional ahpC gene wherein the strain is genetically modified as follows:
i) the thioredoxin reductase encoding gene, trxB is not functional;
ii) the thioredoxin 1 trxA is not functional;
iii) the glutathione reductase gene (gor) is not functional;
iv) an ahpC gene that has been mutated such that it has glutathione reductase activity; and, v) a gene encoding a cytosolic prokaryotic disulfide isomerase has been recombinantly introduced into the bacterial strain.

13. The method of embodiment 12, wherein the E. coli strain contains a null mutation in trxC.

14. The method of any of the embodiments 12-13 wherein the E. coli strain contains a null mutation in trxB.

15. The method of any of the embodiments 12-14 wherein the E. coli strain contains a null mutation in trxA.

16. The method of any of the embodiments 12-15 wherein the protein of interest is selected from the group consisting of: an IgG, a light chain from an IgG or a heavy chain from an IgG.

17. The method of any of the embodiments 12-16 wherein cytosolic disulfide isomerase is DsbC or yeast protein disulfide isomerase (yPDI), or human protein disulfide isomerase (hPDI).

18. The method of any of the embodiments 12-17, wherein the E. coli strain further expresses a recombinant prolyl isomerase and/or a recombinant deaggregase.

19. The method of claim 18 wherein the recombinant prolyl isomerase is selected from the group consisting of: cyclophilin, FKBPs, parvulin, SlyD, Tig and yCpr6; and the deaggregase is selected from the group consisting of Skp, GroEL, GroES, DnaK, DnaJ, and GrpE.

20. The method of any of the embodiments 12-19 wherein the gene encoding the protein of interest is operably linked to a constitutive promoter.

21. The method of any of the embodiments 12-20 wherein the gene encoding the protein of interest is operably linked to a T7 promoter.

22. The method of embodiment 16, wherein the antibody light chain is a light chain of an anti-HER2 antibody.

23. The method of any of the embodiments 12-22 or the E. coli strain of any of the embodiments 1-11, wherein the E. coli strain expresses GshA encoded by the gshA gene.

24. The method of any of the embodiments 12-22 or the E. coli strain of any of the embodiments 1-11, wherein the gshA is inserted into the locus of TrxB.

25. The method of any of the embodiments 12-22 or the E. coli strain of any of the embodiments 1-11, wherein the E. coli strain further express a T7 polymerase.

26. The method of any of the embodiments 12-22 or the E. coli strain of any of the embodiments 1-11, wherein the T7 polymerase is under the control of an inducible promoter.

27. The method of embodiment 26, wherein the inducible prompter is a $P_{araBAD}$, lac, lacUV5, phoA, tetA, xylAB, tac, or rhamnose promoter.

28. A kit comprising the E. coli of any of embodiments 1-11, wherein the kit further comprises a growth medium.

29. The kit of embodiment 27, wherein the kit further comprises a plasmid encoding a protein of interest.

Example 1. General Methods

All genomic manipulations, knock-ins and knock-outs, were performed with a modified site-specific recombination protocol from Kirill A. Datsenko and Barry L. Wanner Proc Natl Acad Sci USA. 2000 Jun. 6; 97(12): 6640-6645. These methods allow exchange to occur at a specific site, as in the integration of the genes of interest that are to be knocked in and the excision of genes to be knocked out from it. Site specific recombination involves specific, inverted repeat sequences, e.g., the Cre-LoxP systems. For insertions, the integration cassette, was composed of the gene, e.g., DsbC (NP_417369), to be inserted adjacent to a selectable marker that is flanked by loxP sites. After the entire cassette was knocked onto the chromosome, the selectable marker gene was subsequently eliminated by transient exposure to Cre recombinase that was effected by electroporation by a plasmid encoding Cre recombinase, while leaving the gene of interest integrated in the genome. For knock outs, the deletion cassette, was composed of a selectable marker that is flanked by loxP sites. After the cassette was knocked onto the chromosome, the selectable marker gene was subsequently eliminated by transient exposure to Cre recombinase that was effected by electroporation by a plasmid encoding Cre recombinase.

Example 2. Production of Snuggle Strain

The background for all strains with oxidative cytoplasm is S97. This strain has all the mutations present in strain KGK10 (Knapp K G, Goerke A R and Swartz J, Biotechnol Bioeng. 2007 Jul. 1; 97(4):901-8) with ompT sensitive RF1 developed to facilitate NNAA incorporation in cell free protein synthesis systems, (Yin et al, Sci Rep. 2017 Jun. 8; 7(1):3026). In addition, this strain has a chromosomal copy of the T7 RNA polymerase that has been chromosomally integrated under the control of the ParaBAD promoter for tightly controlled expression of proteins from the strong T7 promoter. Viability of all strains produced as described below were checked using a plate assay essentially as described in Ritz et al, Science, 2001, with the following modifications. Cells were plated directly on rich media plates after chromosomal modifications.

Five additional mutations were introduced into the S97 strain. These mutations were responsible for the production of an alternative reductive pathway for small molecules which is required for viability in the absence of thioredoxin reductase or glutathione reductase. First, an ahpC variant was introduced by knocking in a mutant variant of ahpC gene, ahpC* into the Frt recombinase scar left in the tnaA locus from deletion of that gene. This gene was tested under the control of a weak promoter PL57 or a medium strength promoter Pc0. As shown in Table 2, as compared to the wild type ahpC gene, which encodes a wild type protein containing two phenylalanines at residues 36 and 37, the ahpC* encodes a mutein comprising three phenylalanines at this location. The ahpC* mutein loses peroxyreductase activity (as exhibited by the wild type ahpC protein), but gains glutathione reductase activity. ahpCΔ, has only one phenylalanine at this location and does not encode a functional peroxyreductase. The ahpCΔ mutant has been reported to restore growth to the mutant B strains of E. coli lacking trxB and gor, ("B strain").

Second, a gshA gene, which was previously deleted from a precursor strain of E. coli, was knocked into the trxB of the mutant strain generated above under the weak promoter PL59 or an intermediate strength WT gshA promoter. Viable combinations were obtained with either promoter. This had the simultaneous effect of completing the new AhpC*-glutathione reduction pathway, and eliminating the thioredoxin-mediated pathway. We anticipated that the expression levels for these proteins would be important for establishing a viable alternative reduction pathway.

Viable combinations were achieved with gshA knock-ins with either PL59 or WT gshA promoter. However, only cells harboring ahpC* with the Pc0 promoter (as described in www.ncbi.nlm.nih.gov/pmc/articles/PMC1134079) were viable, indicating that higher levels of this protein are crucial, while a wider concentration range of GshA is sufficient for growth. This strain produced above contained three different mutations, ahpC* and gshA knock-ins and trxB knockout, which is sufficient for producing an oxidative cytoplasm capable of disulfide formation.

Third, a leaderless DsbC gene was knocked into the chromosome with a strong MTL promoter. The leaderless DsbC protein lacks a secretion signal peptide and functions as a disulfide isomerase in the cytoplasm, which promotes native disulfide assembly of cytoplasmic proteins. Thus, the strain so produced, with these three mutations, i.e., trxB knock out, DsbC knock-in and an ahpC* mutation, referred to as the "Shuffle," was capable of LC folding assembly.

The mutations required to produce Shuffle E. coli, although reported to have produce high titers of disulfide bonded mammalian proteins in other reports, did not lead to high level LC production here. A fourth mutation was thus introduced to solve the problem, by knocking out the thioredoxin 1 (TrxA). This mutation resulted in the desired LC strain capable of expressing all LC at high levels. Strains that lack any one of these modifications were not able to produce as much of the LCs. This new strain ("419" as shown in Table 2), having the all five mutations, named "Snuggle", produced yields higher than previous "Shuffle" strains for production of disulfide bonded proteins. This result is particularly surprising given that the primary reductase for TrxA, TrxB, has already been deleted, and so TrxA should not have been functional as a cytoplasmic reductase.

Disulfide bond formation and reduction is a dynamic process influenced by both pro-oxidative proteins and small molecules such as DsbA and $O_2$ and pro-reductive proteins and small molecules such as cysteine and thioredoxin. Because of this, it is difficult to say how much activity of a given protein is required to produce a given phenotype. That being said, drastically lower LC production potential were observed for LCs that are difficult to produce when TrxB, TrxA, were present or when DsbC was not present. Such striking differences indicate that even a little trxA or trxB activity would likely be sufficient to disrupt the redox environment of the cytosol and LC folding to some extent. It is expected that for trxA or trxB, a protein expression or activity level >25% of endogenous levels would cause deleterious effects. For 1DsbC, cytoplasmic concentration required for LC folding is less clear because Snuggle and Shuffle use different promoters for cytosolic DsbC production. Because this functions as a chaperone and disulfide isomerase it still probably requires overexpression of this protein, at levels at least 25% of that present in Snuggle.

Seven E. coli strains, generated as described in Example 2, were confirmed to have the phenotypes listed in the Table 1, below:

TABLE 1

Strain phenotypes

|  | Shuffle | 347 | 410 | 413 | 414 | 417 | 419 |
|---|---|---|---|---|---|---|---|
| trxB delta (ahpC*, gshA⁺) | + | — | + | + | — | + | + |
| trxA delta | — | — | — | + | — | — | + |
| Cyt. DsbC | + | — | — | — | + | + | + |

"+" represent the mutation as described on the first column, the corresponding row was present.

Each strain was transformed with plasmid pJ411 from Atum (Newwark, Calif.) containing a LC gene (Muc1 G09k LC, 7219 LC, or Trastuzumab LC), codon optimized for E. coli expression. Cells were grown overnight at 37° C. in Terrific Broth (TB) (Thermo Fisher Scientific, Waltham, Mass.) supplemented with 40 mg/L Kanamycin. The next day, cells were diluted 1:100 into fresh TB with Kanamycin and grown at 37° C. until an OD of 2.0. At that point, cells were induced by the addition of 0.2% arabinose and moved to 25° C. After an overnight induction, cells were harvested in the morning. Cells were re-suspended in BPER bacterial lysis reagent (Thermo Fisher Scientific, Waltham, Mass.) with 1 μl/ml benzonase nuclease and 10 mg/ml hen eggwhite lysozyme to release soluble, cytoplasmic protein. 100 μl of total cell lysate was transferred to a new tube, and cell debris and insoluble protein were pelleted by centrifugation at 20,000×G for 10 minutes. The supernatant containing the soluble proteins was transferred to a new tube. The pellet was then re-suspended and dissolved in 100 μl 1×LDS sample buffer. For analysis of LC in each fraction, 10 μl of soluble and insoluble protein samples were loading onto a NuPAGE SDS gel and run until the dye front was at the bottom of the gel. Gels were stained with simply blue safe stain, de-stained with water and then imaged with a Biorad GelDoc EZ. Gel intensity and relative protein quantification were determined using densitometry.

FIG. 1A shows the expression profile for a poorly behaved LC, the light chain of the anti-Muc1 antibody Muc1 G09k LC. Muc1 G09k LC is also known as HT186-D11 and is described in Thie et al., PloS One, 2011 Jan. 14; 6 (1): e15921, the relevant disclosure is herein incorporated by reference. For these samples, the commercially available Shuffle strain give reasonable production of soluble protein. Not surprisingly, all mutants with reducing cytoplasm, or those lacking cytosolic DsbC failed to produce LC in reasonable titer. Surprisingly, the Sutro strain mutant (S417) with a genotype analogous to Shuffle including cytosolic DsbC and oxidative cytoplasm failed to express this LC at reasonable titers. However, S419, which contained the additional mutation of TrxA, enabled LC production at levels higher than the Shuffle strain indicating that the suite of changes made to this strain made it a superior host for LC production.

Figure 1B:
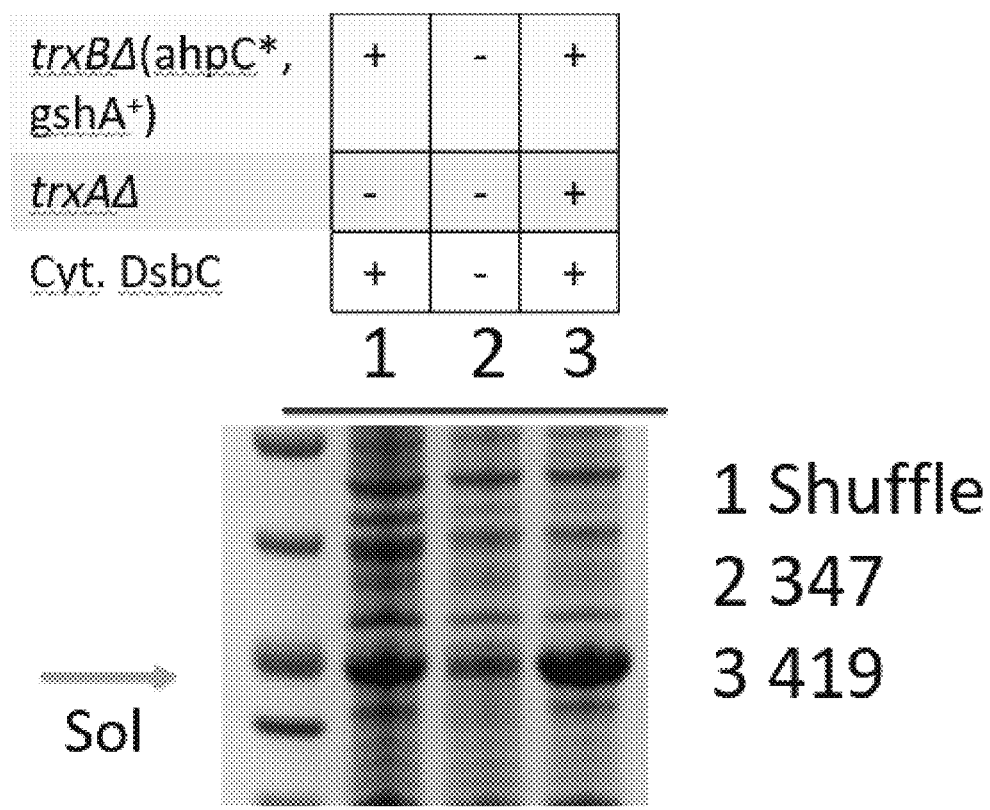
FIG. 1B shows the results of the SDS-PAGE analysis of the soluble fraction of the cell lysates from three modified *E. coli* strains expressing the 7219 LC, the light chain of the anti CD74 IgG. The genotypes of these *E. coli* strains are shown in the table above the SDS-PAGE results.

FIG. 1B shows another example of a challenging LC, 7219 LC made in Shuffle cells, a precursor Sutro strain with reducing cytoplasm and Snuggle. 7219 LC is an anti CD74 IgG, as described in WO/2016/014434, the entire disclosure of which is herein incorporated by reference. For these samples, only the soluble protein was analyzed with the method above. Again, we see very little LC expression in the strain with reducing cytoplasm, while the Snuggle strain produces visibly higher titers than the Shuffle strain.

Figure 1C:
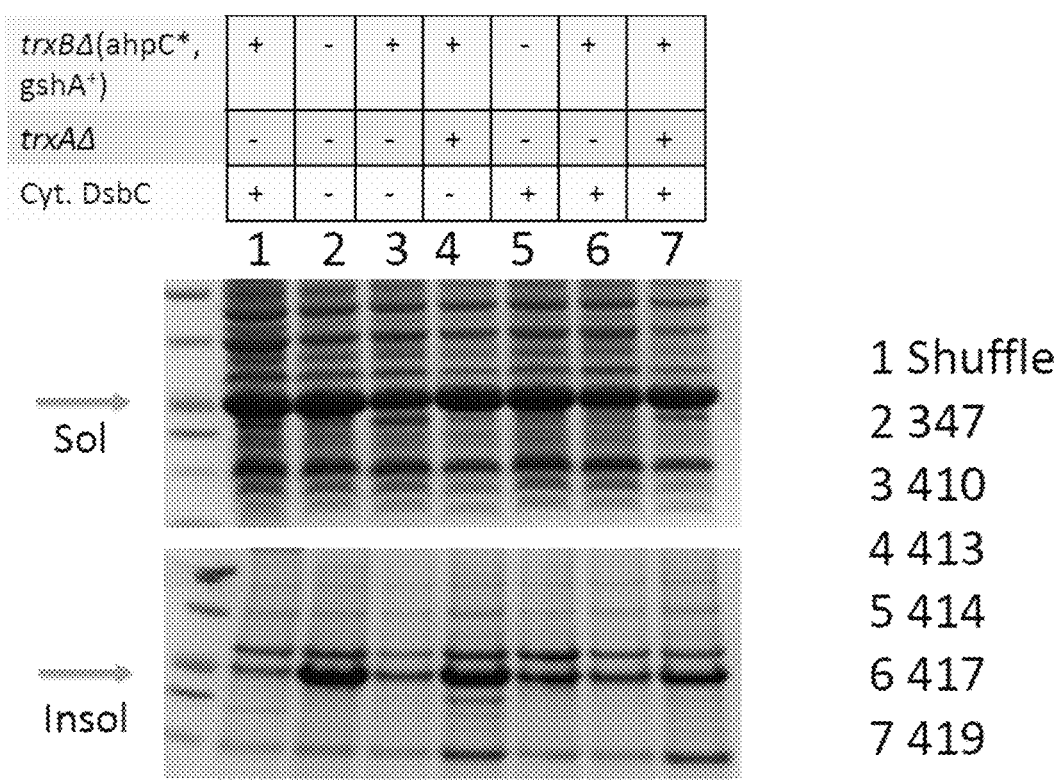
FIG. 1C shows the results of SDS-PAGE analysis similar to that in FIG. 1A, except that the LC being expressed is the light chain of trastuzumab, a protein that is relatively easy to express.

FIG. 1C shows an example of a LC that is relatively easier to produce in E. coli, trastuzumab LC. For this LC there was an excellent soluble expression regardless of host. In this case, the LC does not need disulfide bonding for folding or stability. There was very little LC that ends up in the insoluble fraction.

Example 3. Mutant AHPC that Restore Growth in ΔGOR/TRXB Strains

The wild type AhpC protein is a peroxyreductase, containing two phenylalanines at residues 36 and 37. See the last row in Table 2. The mutation that restores growth in K12 based strains, AhpC* is shown at the third row in Table 2. The AhpC* mutant strain contained an additional phenylalanine residue inserted in between the two phenylalanines at residues 36 and 37. The ahpC mutant that is reported to restore growth to B strains, AhpC Δ, is shown in the middle. The ahpC mutant strain has only one phenylalanine as shown in Table 2; for convenience, residue 37 is shown as deleted but in principle the deletion could be assigned to either residue 36 or 37. During the production of the Snuggle strain, either mutant was introduced onto the chromosome of E. coli K12 derived cells with deletions in gor and trxB. Only the AhpC* mutant restored viability in these cells, which is believed to be because this strain has a K12 lineage.

TABLE 2

| Strain | AhpC mutant | amino acid # | 34 Ser | 35 Val | 36 Phe | | 37 Phe | 38 Phe | 39 Tyr | 40 Pro |
|---|---|---|---|---|---|---|---|---|---|---|
| | | amino acid | | | | | | | | |
| K12 Δgor/trxB | ahpC* | | AGC | GTC | TTC | TTC | TTC | TTC | TAC | CCG |
| BL21 Δgor/trxB | ahpCΔ | | AGC | GTC | TTC | | | TTC | TAC | CCG |
| WT B and K12 | WT | | AGC | GTC | TTC | | TTC | TTC | TAC | CCG |

The AhpC mutant was analyzed to determine whether it had glutathione reductase activity based on its ability to convert oxidized glutathione (GSSG) into reduced glutathione (GSH). The method is described in Yamamoto et al., Mol. Cell. January 18; 29(1): 36-45 (2008). Briefly, purified AhpC mutein at 5 µM were incubated with a reaction mixture containing 1 mM GSSG, 0.5 µM of the protein Alkyl hydroperoxide reductase subunit F (AhpF), 10 µM of the protein glutaredoxin 1 (grxA) and 0.8 mM NADH. The results show that the AhpC* mutant generated free glutathione, GSH, indicating that the mutant possesses glutathione reductase activity. The WT protein and the ahpC delta mutant lacking this activity were unable to produce GSH from GSSG.

Example 4. Recombinant LC Expression in Shuffle and Snuggle E. coli Strains

Plasmids encoding four distinct LCs (LC-1, LC-2, LC-3, and LC-4) were transformed into the Shuffle E. coli strain (C3026J, New England Biosciences) and Snuggle E. coli strain produced as described in Example 2. These four LCs share 78-92% sequence identity with each other. Cells were grown in TB at 37° C. to an OD of 1.5 in a shake flask and induced with 0.1% Arabinose (Snuggle) or 1% Arabinose and 1 mM IPTG (Shuffle). Protein expression was carried out for 16 hrs at 25° C. Cells were harvested by centrifugation of 1 mL of the fermentation media at 21,000×g for 10 min in a benchtop centrifuge. The resulting pellet was resuspended and lysed in B-PER Bacterial Protein Extraction Reagent (78248, Thermo Fisher) containing 50 mg/L Lysozyme (L6876, Sigma Aldrich) and 25 U/mL Benzonase (E1014, Sigma Aldrich) at a ratio of 10 mL per g of wet cell weight. Insoluble material was removed by centrifugation at 21,000×g for 10 min in a benchtop centrifuge. A reducing SDS page gel was run with 4 uL of the resulting lysate per well and the relative expression of Coomassie stained LC bands was determined by gel densitometry.

Figure 2:
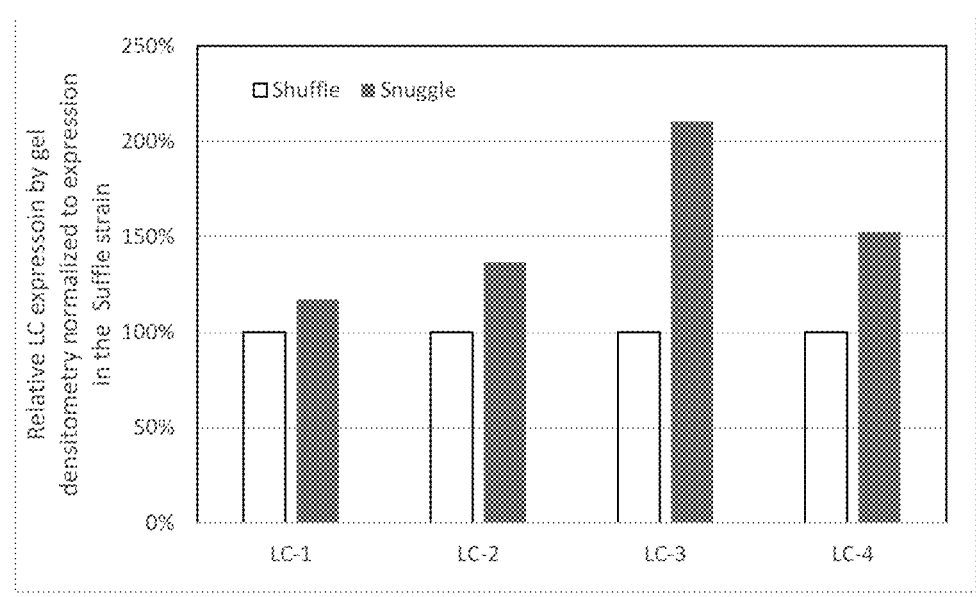
FIG. 2 shows the results of relative expression of 4 distinct LCs with 78-92% sequence identity in the Shuffle and Snuggle *E. coli* strains. The Snuggle strain showed between 20-110% improvement in LC production compared to the Shuffle strain.

As shown in FIG. 2, the Snuggle strain demonstrated between 20-110% improvement in LC production in terms of yield compared to the Shuffle strain.

```
ILLUSTRATIVE SEQUENCES
SEQ ID NO: 1 dsbC nucleic acid sequence
atgAAGAAAG GTTTTATGTT GTTTACTTTG TTAGCGGCGT TTTCAGGCTT TGCTCAGGCT

GATGACGCGG CAATTCAACA AACGTTAGCC AAAATGGGCA TCAAAAGCAG CGATATTCAG

CCCGCGCCTG TAGCTGGCAT GAAGACAGTT CTGACTAACA GCGGCGTGTT GTACATCACC

GATGATGGTA ACATATCAT TCAGGGGCCA ATGTATGACG TTAGTGGCAC GGCTCCGGTC

AATGTCACCA ATAAGATGCT GTTAAAGCAG TTGAATGCGC TTGAAAAAGA GATGATCGTT

TATAAAGCGC GCAGGAAAA ACACGTCATC ACCGTGTTTA CTGATATTAC CTGTGGTTAC

TGCCACAAAC TGCATGAGCA AATGGCAGAC TACAACGCGC TGGGGATCAC CGTGCGTTAT

CTTGCTTTCC CGCGCCAGGG GCTGGACAGC GATGCAGAGA AAGAAATGAA AGCTATCTGG

TGTGCGAAAG ATAAAAACAA AGCGTTTGAT GATGTGATGG CAGGTAAAAG CGTCGCACCA

GCCAGTTGCG ACGTGGATAT TGCCGACCAT TACGCACTTG GCGTCCAGCT TGGCGTTAGC

GGTACTCCGG CAGTTGTGCT GAGCAATGGC ACACTTGTTC CGGGTTACCA GCCGCCGAAA

GAGATGAAAG AATTCCTGA CGAACACCAA AAAATGACCA GCGGTAAAta a

SEQ ID NO: 2. ahpC nucleic acid sequence
atgTCCTTGA TTAACACCAA AATTAAACCT TTTAAAAACC AGGCATTCAA AAACGGCGAA

TTCATCGAAA TCACCGAAAA AGATACCGAA GGCCGCTGGA GCGTCTTCTT CTTCTACCCG

GCTGACTTTA CTTTCGTATG CCCGACCGAA CTGGGTGACG TTGCTGACCA CTACGAAGAA

CTGCAGAAAC TGGGCGTAGA CGTATACGCA GTATCTACCG ATACTCACTT CACCCACAAA

GCATGGCACA GCAGCTCTGA AACCATCGCT AAAATCAAAT ATGCGATGAT CGGCGACCCG

ACTGGCGCCC TGACCCGTAA CTTCGACAAC ATGCGTGAAG ATGAAGGTCT GGCTGACCGT

GCGACCTTCG TTGTTGACCC GCAGGGTATC ATCCAGGCAA TCGAAGTTAC CGCTGAAGGC
```

-continued

ATTGGCCGTG ACGCGTCTGA CCTGCTGCGT AAAATCAAAG CAGCACAGTA CGTAGCTTCT

CACCCAGGTG AAGTTTGCCC GGCTAAATGG AAAGAAGGTG AAGCAACTCT GGCTCCGTCT

CTGGACCTGG TTGGTAAAAT Ctaa

SEQ ID NO: 3 ahpC protein sequence
MSLINTKIKP FKNQAFKNGE FIEITEKDTE GRWSVFFFYP ADFTFVCPTE LGDVADHYEE

LQKLGVDVYA VSTDTHFTHK AWHSSSETIA KIKYAMIGDP TGALTRNFDN MREDEGLADR

ATFVVDPQGI IQAIEVTAEG IGRDASDLLR KIKAAQYVAS HPGEVCPAKW KEGEATLAPS

LDLVGKI

SEQ ID NO: 4 ahpC* nucleic acid sequence (codon optimized for
expression in E. coli)
ATGAGCCTGATCAACACGAAAATCAAGCCGTTCAAGAACCAAGCTTTCAAAAATGGTGAGTTCATCGAGA

TTACCGAGAAAGATACCGAGGGTCGTTGGAGCGTGTTCTTCTTCTTTTATCCGGCGGACTTTACTTTTGT

TTGTCCTACCGAGCTGGGTGACGTTGCGGACCATTATGAAGAACTGCAGAAATTGGGCGTCGACGTTTAC

GCCGTCAGCACGGACACGCACTTTACGCACAAGGCATGGCACTCTAGCAGCGAAACCATCGCAAAGATCA

AATACGCAATGATTGGCGACCCGACGGGTGCACTGACCCGCAATTTCGATAACATGCGTGAAGATGAAGG

CCTGGCGGATCGTGCGACCTTCGTCGTGGACCCGCAGGGTATCATTCAGGCTATCGAAGTTACCGCCGAG

GGTATTGGTCGTGATGCGAGCGATCTGCTGCGCAAGATTAAAGCCGCGCAATACGTTGCATCCCATCCGG

GCGAAGTGTGCCCAGCCAAGTGGAAAGAGGGCGAGGCGACCCTGGCGCCGAGCCTGGACTTGGTGGGTAA

GATT

SEQ ID NO: 5 AhpC* protein sequence
MSLINTKIKP FKNQAFKNGE FIEITEKDTE GRWSVFFFYP ADFTFVCPTE LGDVADHYEE

LQKLGVDVYA VSTDTHFTHK AWHSSSETIA KIKYAMIGDP TGALTRNFDN MREDEGLADR

ATFVVDPQGI IQAIEVTAEG IGRDASDLLR KIKAAQYVAS HPGEVCPAKW KEGEATLAPS

LDLVGKI

SEQ ID NO: 6 DsbC protein sequence (the underlined is the signal
sequence)
<u>MKKGFMLFTL LAAFSGFAQA</u> DDAAIQQTLA KMGIKSSDIQ PAPVAGMKTV LTNSGVLYIT

DDGKHIIQGP MYDVSGTAPV NVTNKMLLKQ LNALEKEMIV YKAPQEKHVI TVFTDITCGY

CHKLHEQMAD YNALGITVRY LAFPRQGLDS DAEKEMKAIW CAKDKNKAFD DVMAGKSVAP

ASCDVDIADH YALGVQLGVS GTPAVVLSNG TLVPGYQPPK EMKEFLDEHQ KMTSGK

SEQ ID NO: 7 trxA nucleic acid sequence
atgAGCGATA AAATTATTCA CCTGACTGAC GACAGTTTTG ACACGGATGT ACTCAAAGCG

GACGGGGCGA TCCTCGTCGA TTTCTGGGCA GAGTGGTGCG GTCCGTGCAA AATGATCGCC

CCGATTCTGG ATGAAATCGC TGACGAATAT CAGGGCAAAC TGACCGTTGC AAAACTGAAC

ATCGATCAAA ACCCTGGCAC TGCGCCGAAA TATGGCATCC GTGGTATCCC GACTCTGCTG

CTGTTCAAAA ACGGTGAAGT GGCGGCAACC AAAGTGGGTG CACTGTCTAA AGGTCAGTTG

AAAGAGTTCC TCGACGCTAA CCTGGCGtaa

SEQ ID NO: 8 trxA protein sequence
MSDKIIHLTD DSFDTDVLKA DGAILVDFWA EWCGPCKMIA PILDEIADEY QGKLTVAKLN

IDQNPGTAPK YGIRGIPTLL LFKNGEVAAT KVGALSKGQL KEFLDANLA

SEQ ID NO: 9 trxB nucleic acid sequence
atgGGCACGA CCAAACACAG TAAACTGCTT ATCCTGGGTT CAGGCCCGGC GGGATACACC

GCTGCTGTCT ACGCGGCGCG CGCCAACCTG CAACCTGTGC TGATTACCGG CATGGAAAAA

GGCGGCCAAC TGACCACCAC CACGGAAGTG GAAAACTGGC CTGGCGATCC AAACGATCTG

ACCGGTCCGT TATTAATGGA GCGCATGCAC GAACATGCCA CCAAGTTTGA AACTGAGATC

-continued

```
ATTTTTGATC ATATCAACAA GGTGGATCTG CAAAACCGTC CGTTCCGTCT GAATGGCGAT

AACGGCGAAT ACACTTGCGA CGCGCTGATT ATTGCCACCG GAGCTTCTGC ACGCTATCTC

GGCCTGCCCT CTGAAGAAGC CTTTAAAGGC CGTGGGGTTT CTGCTTGTGC AACCTGCGAC

GGTTTCTTCT ATCGCAACCA GAAAGTTGCG GTCATCGGCG GCGGCAATAC CGCGGTTGAA

GAGGCGCTGT ATCTGTCTAA CATCGCTTCG GAAGTGCATC TGATTCACCG CCGTGACGGT

TTCCGCGCGG AAAAAATCCT CATTAAGCGC CTGATGGATA AGTGGAGAA CGGCAACATC

ATTCTGCACA CCAACCGTAC GCTGGAAGAA GTGACCGGCG ATCAAATGGG TGTCACTGGC

GTTCGTCTGC GCGATACGCA AAACAGCGAT AACATCGAGT CACTCGACGT TGCCGGTCTG

TTTGTTGCTA TCGGTCACAG CCCGAATACT GCGATTTTCG AAGGGCAGCT GGAACTGGAA

AACGGCTACA TCAAAGTACA GTCGGGTATT CATGGTAATG CCACCCAGAC CAGCATTCCT

GGCGTCTTTG CCGCAGGCGA CGTGATGGAT CACATTTATC GCCAGGCCAT TACTTCGGCC

GGTACAGGCT GCATGGCAGC ACTTGATGCG AACGCTACC TCGATGGTTT AGCTGACGCA

AAAtaa

SEQ ID NO: 10 trxB protein sequence
MGTTKHSKLL ILGSGPAGYT AAVYAARANL QPVLITGMEK GGQLTTTTEV ENWPGDPNDL

TGPLLMERMH EHATKFETEI IFDHINKVDL QNRPFRLNGD NGEYTCDALI IATGASARYL

GLPSEEAFKG RGVSACATCD GFFYRNQKVA VIGGGNTAVE EALYLSNIAS EVHLIHRRDG

FRAEKILIKR LMDKVENGNI ILHTNRTLEE VTGDQMGVTG VRLRDTQNSD NIESLDVAGL

FVAIGHSPNT AIFEGQLELE NGYIKVQSGI HGNATQTSIP GVFAAGDVMD HIYRQAITSA

GTGCMAALDA ERYLDGLADA K

SEQ ID NO: 11 Gor nucleic acid sequence
atgACTAAAC ACTATGATTA CATCGCCATC GGCGGCGGCA GCGGCGGTAT CGCCTCCATC

AACCGCGCGG CTATGTACGG CCAGAAATGT GCGCTGATTG AAGCCAAAGA GCTGGGCGGC

ACCTGCGTAA ATGTTGGCTG TGTGCCGAAA AAAGTGATGT GGCACGCGGC GCAAATCCGT

GAAGCGATCC ATATGTACGG CCCGGATTAT GGTTTTGATA CCACTATCAA TAAATTCAAC

TGGGAAACGT TGATCGCCAG CCGTACCGCC TATATCGACC GTATTCATAC TTCCTATGAA

AACGTGCTCG GTAAAAATAA CGTTGATGTA ATCAAAGGCT TTGCCCGCTT CGTTGATGCC

AAAACGCTGG AGGTAAACGG CGAAACCATC ACGGCCGATC ATATTCTGAT CGCCACAGGC

GGTCGTCCGA GCCACCCGGA TATTCCGGGC GTGGAATACG GTATTGATTC TGATGGCTTC

TTCGCCCTTC CTGCTTTGCC AGAGCGCGTG GCGGTTGTTG GCGCGGGTTA CATCGCCGTT

GAGCTGGCGG GCGTGATTAA CGGCCTCGGC GCGAAAACGC ATCTGTTTGT GCGTAAACAT

GCGCCGCTGC GCAGCTTCGA CCCGATGATT TCCGAAACGC TGGTCGAAGT GATGAACGCC

GAAGGCCCGC AGCTGCACAC CAACGCCATC CCGAAAGCGG TAGTGAAAAA TACCGATGGT

AGCCTGACGC TGGAGCTGGA AGATGGTCGC AGTGAAACGG TGGATTGCCT GATTTGGGCG

ATTGGTCGCG AGCCTGCCAA TGACAACATC AACCTGGAAG CCGCTGGCGT TAAAACTAAC

GAAAAAGGCT ATATCGTCGT CGATAAATAT CAAACACCA ATATTGAAGG TATTTACGCG

GTGGGCGATA ACACGGGTGC AGTGGAGCTG ACACCGGTGG CAGTTGCAGC GGGTCGCCGT

CTCTCTGAAC GCCTGTTTAA TAACAAGCCG GATGAGCATC TGGATTACAG CAACATTCCG

ACCGTGGTCT TCAGCCATCC GCCGATTGGT ACTGTTGGTT TAACGGAACC GCAGGCGCGC

GAGCAGTATG GCGACGATCA GGTGAAAGTG TATAAATCCT CTTTCACCGC GATGTATACC

GCCGTCACCA CTCACCGCCA GCCGTGCCGC ATGAAGCTGG TGTGCGTTGG ATCGGAAGAG

AAGATTGTCG GTATTCACGG CATTGGCTTT GGTATGGACG AAATGTTGCA GGGCTTCGCG
```

```
GTGGCGCTGA AGATGGGGGC AACCAAAAAA GACTTCGACA ATACCGTCGC CATTCACCCA

ACGGCGGCAG AAGAGTTCGT GACAATGCGT taa
```

SEQ ID NO: 12 Gor protein sequence
```
MTKHYDYIAI GGGSGGIASI NRAAMYGQKC ALIEAKELGG TCVNVGCVPK KVMWHAAQIR

EAIHMYGPDY GFDTTINKFN WETLIASRTA YIDRIHTSYE NVLGKNNVDV IKGFARFVDA

KTLEVNGETI TADHILIATG GRPSHPDIPG VEYGIDSDGF FALPALPERV AVVGAGYIAV

ELAGVINGLG AKTHLFVRKH APLRSFDPMI SETLVEVMNA EGPQLHTNAI PKAVVKNTDG

SLTLELEDGR SETVDCLIWA IGREPANDNI NLEAAGVKTN EKGYIVVDKY QNTNIEGIYA

VGDNTGAVEL TPVAVAAGRR LSERLFNNKP DEHLDYSNIP TVVFSHPPIG TVGLTEPQAR

EQYGDDQVKV YKSSFTAMYT AVTTHRQPCR MKLVCVGSEE KIVGIHGIGF GMDEMLQGFA

VALKMGATKK DFDNTVAIHP TAAEEFVTMR
```

SEQ ID NO: 13 gshA nucleic acid sequence
```
ttgATCCCGG ACGTATCACA GGCGCTGGCC TGGCTGGAAA ACATCCTCA GGCGTTAAAG

GGGATACAGC GTGGGCTGGA GCGCGAAACT TGCGTGTTA ATGCTGATGG CACACTGGCA

ACAACAGGTC ATCCTGAAGC ATTAGGTTCC GCACTGACGC ACAAATGGAT TACTACCGAT

TTTGCGGAAG CATTGCTGGA ATTCATTACA CCAGTGGATG GTGATATTGA ACATATGCTG

ACCTTTATGC GCGATCTGCA TCGTTATACG GCGCGCAATA TGGGCGATGA GCGGATGTGG

CCGTTAAGTA TGCCATGCTA CATCGCAGAA GGTCAGGACA TCGAACTGGC ACAGTACGGC

ACTTCTAACA CCGGACGCTT TAAAACGCTG TATCGTGAAG GGCTGAAAAA TCGCTACGGC

GCGCTGATGC AAACCATTTC CGGCGTGCAC TACAATTTCT CTTTGCCAAT GGCATTCTGG

CAAGCGAAGT GCGGTGATAT CTCGGGCGCT GATGCCAAAG AGAAAATTTC TGCGGGCTAT

TTCCGCGTTA TCCGCAATTA CTATCGTTTC GGTTGGGTCA TTCCTTATCT GTTTGGTGCA

TCTCCGGCGA TTTGTTCTTC TTTCCTGCAA GGAAAACCAA CGTCGCTGCC GTTTGAGAAA

ACCGAGTGCG GTATGTATTA CCTGCCGTAT GCGACCTCTC TTCGTTTGAG CGATCTCGGC

TATACCAATA AATCGCAAAG CAATCTTGGT ATTACCTTCA ACGATCTTTA CGAGTACGTA

GCGGGCCTTA ACAGGCAAT CAAAACGCCA TCGGAAGAGT ACGCGAAGAT TGGTATTGAG

AAAGACGGTA AGAGGCTGCA ATCAACAGC AACGTGTTGC AGATTGAAAA CGAACTGTAC

GCGCCGATTC GTCCAAAACG CGTTACCCGC AGCGGCGAGT CGCCTTCTGA TGCGCTGTTA

CGTGGCGGCA TTGAATATAT TGAAGTGCGT TCGCTGGACA TCAACCCGTT CTCGCCGATT

GGTGTAGATG AACAGCAGGT GCGATTCCTC GACCTGTTTA TGGTCTGGTG TGCGCTGGCT

GATGCACCGG AAATGAGCAG TAGCGAACTT GCCTGTACAC GCGTTAACTG GAACCGGGTG

ATCCTCGAAG GTCGCAAACC GGGTCTGACG CTGGGTATCG GCTGCGAAAC CGCACAGTTC

CCGTTACCGC AGGTGGGTAA AGATCTGTTC CGCGATCTGA AACGCGTCGC GCAAACGCTG

GATAGTATTA ACGGCGGCGA AGCGTATCAG AAAGTGTGTG ATGAACTGGT TGCCTGCTTC

GATAATCCCG ATCTGACTTT CTCTGCCCGT ATCTTAAGGT CTATGATTGA TACTGGTATT

GGCGGAACAG GCAAAGCATT TGCAGAAGCC TACCGTAATC TGCTGCGTGA AGAGCCGCTG

GAAATTCTGC GCGAAGAGGA TTTTGTAGCC GAGCGCGAGG CGTCTGAACG CCGTCAGCAG

GAAATGGAAG CCGCTGATAC CGAACCGTTT GCGGTGTGGC TGGAAAAACA CGCCtga
```

SEQ ID NO: 14 gshA protein sequence
```
MIPDVSQALA WLEKHPQALK GIQRGLERET LRVNADGTLA TTGHPEALGS ALTHKWITTD

FAEALLEFIT PVDGDIEHML TFMRDLHRYT ARNMGDERMW PLSMPCYIAE GQDIELAQYG

TSNTGRFKTL YREGLKNRYG ALMQTISGVH YNFSLPMAFW QAKCGDISGA DAKEKISAGY
```

-continued

FRVIRNYYRF GWVIPYLFGA SPAICSSFLQ GKPTSLPFEK TECGMYYLPY ATSLRLSDLG

YTNKSQSNLG ITFNDLYEYV AGLKQAIKTP SEEYAKIGIE KDGKRLQINS NVLQIENELY

APIRPKRVTR SGESPSDALL RGGIEYIEVR SLDINPFSPI GVDEQQVRFL DLFMVWCALA

DAPEMSSSEL ACTRVNWNRV ILEGRKPGLT LGIGCETAQF PLPQVGKDLF RDLKRVAQTL

DSINGGEAYQ KVCDELVACF DNPDLTFSAR ILRSMIDTGI GGTGKAFAEA YRNLLREEPL

EILREEDFVA EREASERRQQ EMEAADTEPF AVWLEKHA

SEQ ID NO: 15 amino acid sequence of the anti-MUC antibody light chain (HT186-D11-LC)
QSVLTQPPSVSVAPGKTARITCGGNNIGSKSVHWYQQKPGQAPALVIYYGSNRPSGIPERFSGSN

SGNTATLTISRVEAGDEADYYCQVWDSSSDWVFGGGTKLTVL

---

What is claimed is:

1. An *E. coli* strain, wherein:
   i) the strain lacks the activity of a thioredoxin reductase encoded by trxB due to genetic mutation of trxB;
   ii) the strain lacks the activity of a thioredoxin 1 encoded by trxA due to genetic mutation of trxA;
   iii) the strain lacks the activity of a glutathione reductase encoded by gor due to genetic mutation of gor; and
   iv) the strain expresses a mutated AhpC protein, wherein the mutated AhpC protein has glutathione reductase activity.

2. The *E. coli* strain of claim 1, wherein the *E. coli* strain further comprises a gene encoding a protein of interest.

3. The *E. coli* strain of claim 2, wherein the protein of interest is selected from the group consisting of: an antibody, a fragment thereof, and an antibody light chain from an IgG.

4. The *E. coli* strain of claim 1, wherein the mutated AphC protein lacks peroxyreductase activity, and wherein the mutated AphC protein comprises a sequence of SEQ ID NO: 5.

5. The *E. coli* strain of claim 1, wherein the *E. coli* strain has reduced protein expression or mRNA expression of the wild type TrxA, TrxB, and Gor relative to a control *E. coli* strain.

6. The *E. coli* strain of claim 1, wherein the *E. coli* strain expresses a mutated TrxA protein, and wherein the mutated TrxA protein lacks the activity of the corresponding wild-type protein.

7. The *E. coli* strain of claim 1, wherein the *E. coli* strain expresses a mutated TrxB protein, and wherein the mutated TrxB protein lacks the activity of the corresponding wild-type TrxB protein.

8. The *E. coli* strain of claim 1, wherein the *E. coli* strain expresses a mutated Gor protein, and wherein the mutated Gor protein lacks the activity of the corresponding wild type Gor protein.

9. The *E. coli* strain of claim 2, wherein the gene encoding the protein of interest is operably linked to an inducible promoter.

10. The *E. coli* strain of claim 9, wherein the inducible promoter is a T7 promoter.

11. The *E. coli* strain of claim 1, wherein the mutated AphC protein is encoded by a mutated ahpC gene, and wherein the expression of the ahpC gene is controlled by a Pc0 promoter.

12. The *E. coli* strain of claim 1, wherein the *E. coli* strain is a K-12 strain.

13. A method for expressing soluble, recombinant proteins of interest in *E. coli* bacterial strains comprising the steps of:
    culturing an *E. coli* bacterial strain comprising an oxidizing cytosol and an expression cassette for expressing a protein of interest under conditions that permit expression of the protein of interest as a soluble protein, wherein the strain:
    i) lacks thioredoxin reductase activity due to genetic mutation of trxB;
    ii) lacks thioredoxin 1 activity due to genetic mutation of trxA;
    iii) lacks the activity of a glutathione reductase encoded by gor due to genetic mutation of gor; and
    iv) expresses a mutated AhpC protein, wherein the mutated AhpC protein has glutathione reductase activity.

14. The method of claim 13, wherein the mutated AphC protein lacks peroxyreductase activity, and wherein the mutated AphC protein comprises a sequence of SEQ ID NO: 5.

15. The method of claim 13, wherein the *E. coli* strain further expresses a wild-type AhpC protein comprising a sequence of SEQ ID NO: 3.

16. The method of claim 13, wherein the *E. coli* strain has reduced protein expression or mRNA expression of the wild type TrxA, TrxB, and Gor relative to a control *E. coli* strain.

17. The method of claim 13, wherein the *E. coli* strain expresses a mutated TrxA protein, and wherein the mutated TrxA protein lacks the activity of the corresponding wild-type protein.

18. The method of claim 13, wherein the *E. coli* strain expresses a mutated TrxB protein, and wherein the mutated TrxB protein lacks the activity of the wild-type TrxB protein.

19. The method of claim 13, wherein the *E. coli* strain expresses a mutated Gor protein, and wherein the mutated Gor protein lacks the activity of the wild type Gor protein.

20. The method of claim 13, wherein the *E. coli* strain contains a null mutation in one or both of trxB and trxA.

21. The method of claim 13, wherein the protein of interest is selected from the group consisting of: an IgG, a light chain from an IgG, and a heavy chain from an IgG.

22. A kit comprising the *E. coli* of claim 1, wherein the kit further comprises a growth medium.

23. The kit of claim 22, wherein the kit further comprises a plasmid encoding a protein of interest.

* * * * *

SEQUENCE LISTING

<160> NUMBER OF SEQ ID NOS: 15

<210> SEQ ID NO 1
<211> LENGTH: 711
<212> TYPE: DNA
<213> ORGANISM: Escherichia coli

<400> SEQUENCE: 1

```
atgaagaaag gttttatgtt gtttactttg ttagcggcgt tttcaggctt tgctcaggct      60
gatgacgcgg caattcaaca acgttagcc aaaatgggca tcaaaagcag cgatattcag     120
cccgcgcctg tagctggcat gaagacagtt ctgactaaca gcggcgtgtt gtacatcacc     180
gatgatggta acatatcat tcaggggcca atgtatgacg ttagtggcac ggctccggtc     240
aatgtcacca ataagatgct gttaaagcag ttgaatgcgc ttgaaaaaga tgatcgtt      300 tataaagcgc gcaggaaaa acacgtcatc accgtgttta ctgatattac ctgtggttac     360
tgccacaaac tgcatgagca atggcagac tacaacgcgc tggggatcac cgtgcgttat     420
cttgctttcc cgcgccaggg gctggacagc gatgcagaga agaaatgaa agctatctgg     480 tgtgcgaaag ataaaaacaa agcgtttgat gatgtgatgg caggtaaaag cgtcgcacca     540
gccagttgcg acgtggatat tgccgaccat tacgcacttg gcgtccagct tggcgttagc     600
ggtactccgg cagttgtgct gagcaatggc acacttgttc cgggttacca gccgccgaaa     660
gagatgaaag aattcctcga cgaacaccaa aaaatgacca gcggtaaata a              711
```

<210> SEQ ID NO 2
<211> LENGTH: 564
<212> TYPE: DNA
<213> ORGANISM: Escherichia coli

<400> SEQUENCE: 2

```
atgtccttga ttaacaccaa aattaaacct tttaaaaacc aggcattcaa aaacggcgaa      60
ttcatcgaaa tcaccgaaaa agataccgaa ggccgctgga gcgtcttctt cttctacccg     120
gctgacttta ctttcgtatg cccgaccgaa ctgggtgacg ttgctgacca ctacgaagaa     180
ctgcagaaac tgggcgtaga cgtatacgca gtatctaccg atactcactt caccccacaaa     240 gcatggcaca gcagctctga aaccatcgct aaaatcaaat atgcgatgat cggcgacccg     300
actggcgccc tgacccgtaa cttcgacaac atgcgtgaag atgaaggtct ggctgaccgt     360
gcgaccttcg ttgttgaccc gcagggtatc atccaggcaa tcgaagttac cgctgaaggc     420
attggccgtg acgcgtctga cctgctgcgt aaaatcaaag cagcacagta cgtagcttct     480
```
cacccaggtg aagtttgccc ggctaaatgg aaagaaggtg aagcaactct ggctccgtct    540
ctggacctgg ttggtaaaat ctaa    564

<210> SEQ ID NO 3
<211> LENGTH: 187
<212> TYPE: PRT
<213> ORGANISM: Escherichia coli

<400> SEQUENCE: 3

Met Ser Leu Ile Asn Thr Lys Ile Lys Pro Phe Lys Asn Gln Ala Phe
1               5                   10                  15

Lys Asn Gly Glu Phe Ile Glu Ile Thr Glu Lys Asp Thr Glu Gly Arg
            20                  25                  30

Trp Ser Val Phe Phe Phe Tyr Pro Ala Asp Phe Thr Phe Val Cys Pro
        35                  40                  45

Thr Glu Leu Gly Asp Val Ala Asp His Tyr Glu Glu Leu Gln Lys Leu
    50                  55                  60

Gly Val Asp Val Tyr Ala Val Ser Thr Asp Thr His Phe Thr His Lys
65                  70                  75                  80

Ala Trp His Ser Ser Glu Thr Ile Ala Lys Ile Lys Tyr Ala Met
                85                  90                  95

Ile Gly Asp Pro Thr Gly Ala Leu Thr Arg Asn Phe Asp Asn Met Arg
            100                 105                 110

Glu Asp Glu Gly Leu Ala Asp Arg Ala Thr Phe Val Val Asp Pro Gln
        115                 120                 125

Gly Ile Ile Gln Ala Ile Glu Val Thr Ala Glu Gly Ile Gly Arg Asp
    130                 135                 140

Ala Ser Asp Leu Leu Arg Lys Ile Lys Ala Ala Gln Tyr Val Ala Ser
145                 150                 155                 160

His Pro Gly Glu Val Cys Pro Ala Lys Trp Lys Glu Gly Glu Ala Thr
                165                 170                 175

Leu Ala Pro Ser Leu Asp Leu Val Gly Lys Ile
            180                 185

<210> SEQ ID NO 4
<211> LENGTH: 564
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
atgagcctga tcaacacgaa atcaagccg ttcaagaacc aagctttcaa aaatggtgag    60
ttcatcgaga ttaccgagaa agataccgag gtcgttgga gcgtgttctt cttcttttat   120
ccggcggact ttacttttgt ttgtcctacc gagctgggtg acgttgcgga ccattatgaa   180
gaactgcaga aattgggcgt cgacgtttac gccgtcagca cggacacgca ctttacgcac   240
aaggcatggc actctagcag cgaaaccatc gcaaagatca atacgcaat gattggcgac   300 ccgacgggtg cactgacccg caatttcgat aacatgcgtg aagatgaagg cctggcggat   360
cgtgcgacct tcgtcgtgga cccgcagggt atcattcagg ctatcgaagt taccgccgag   420
ggtattggtc gtgatgcgag cgatctgctg cgcaagatta agccgcgca atacgttgca   480 tcccatccgg gcgaagtgtg cccagccaag tggaaagagg gcgaggcgac cctggcgccg   540
agcctggact tggtgggtaa gatt		564

<210> SEQ ID NO 5
<211> LENGTH: 188
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Met Ser Leu Ile Asn Thr Lys Ile Lys Pro Phe Lys Asn Gln Ala Phe
1               5                   10                  15

Lys Asn Gly Glu Phe Ile Glu Ile Thr Glu Lys Asp Thr Glu Gly Arg
            20                  25                  30

Trp Ser Val Phe Phe Phe Tyr Pro Ala Asp Phe Thr Phe Val Cys
        35                  40                  45

Pro Thr Glu Leu Gly Asp Val Ala Asp His Tyr Glu Glu Leu Gln Lys
    50                  55                  60

Leu Gly Val Asp Val Tyr Ala Val Ser Thr Asp Thr His Phe Thr His
65                  70                  75                  80

Lys Ala Trp His Ser Ser Glu Thr Ile Ala Lys Ile Lys Tyr Ala
                85                  90                  95

Met Ile Gly Asp Pro Thr Gly Ala Leu Thr Arg Asn Phe Asp Asn Met
            100                 105                 110

Arg Glu Asp Glu Gly Leu Ala Asp Arg Ala Thr Phe Val Val Asp Pro
        115                 120                 125

Gln Gly Ile Ile Gln Ala Ile Glu Val Thr Ala Glu Gly Ile Gly Arg
    130                 135                 140

Asp Ala Ser Asp Leu Leu Arg Lys Ile Lys Ala Ala Gln Tyr Val Ala
145                 150                 155                 160

Ser His Pro Gly Glu Val Cys Pro Ala Lys Trp Lys Glu Gly Glu Ala
                165                 170                 175

Thr Leu Ala Pro Ser Leu Asp Leu Val Gly Lys Ile
            180                 185
```

<210> SEQ ID NO 6
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Met Lys Lys Gly Phe Met Leu Phe Thr Leu Leu Ala Ala Phe Ser Gly
1               5                   10                  15

Phe Ala Gln Ala Asp Asp Ala Ile Gln Gln Thr Leu Ala Lys Met
            20                  25                  30

Gly Ile Lys Ser Ser Asp Ile Gln Pro Ala Pro Val Ala Gly Met Lys
        35                  40                  45

Thr Val Leu Thr Asn Ser Gly Val Leu Tyr Ile Thr Asp Asp Gly Lys
    50                  55                  60

His Ile Ile Gln Gly Pro Met Tyr Asp Val Ser Gly Thr Ala Pro Val
65                  70                  75                  80

Asn Val Thr Asn Lys Met Leu Leu Lys Gln Leu Asn Ala Leu Glu Lys
                85                  90                  95
```

```
Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
        115                 120                 125

Ala Asp Tyr Asn Ala Leu Gly Ile Thr Val Arg Tyr Leu Ala Phe Pro
130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
            180                 185                 190

Leu Gly Val Gln Leu Gly Val Ser Gly Thr Pro Ala Val Val Leu Ser
        195                 200                 205

Asn Gly Thr Leu Val Pro Gly Tyr Gln Pro Pro Lys Glu Met Lys Glu
    210                 215                 220

Phe Leu Asp Glu His Gln Lys Met Thr Ser Gly Lys
225                 230                 235
```

```
<210> SEQ ID NO 7
<211> LENGTH: 330
<212> TYPE: DNA
<213> ORGANISM: Escherichia coli

<400> SEQUENCE: 7
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggcgtaa                                    330

<210> SEQ ID NO 8
<211> LENGTH: 109
<212> TYPE: PRT
<213> ORGANISM: Escherichia coli

<400> SEQUENCE: 8

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 9
```

```
<211> LENGTH: 966
<212> TYPE: DNA
<213> ORGANISM: Escherichia coli

<400> SEQUENCE: 9
atgggcacga ccaaacacag taaactgctt atcctgggtt caggcccggc gggatacacc      60
gctgctgtct acgcggcgcg cgccaacctg caacctgtgc tgattaccgg catggaaaaa     120
ggcggccaac tgaccaccac cacggaagtg gaaaactggc ctggcgatcc aaacgatctg     180
accggtccgt tattaatgga gcgcatgcac gaacatgcca ccaagtttga aactgagatc     240 attttgatc atatcaacaa ggtggatctg caaaaccgtc cgttccgtct gaatggcgat     300
aacggcgaat acacttgcga cgcgctgatt attgccaccg gagcttctgc acgctatctc     360
ggcctgccct ctgaagaagc ctttaaaggc cgtggggttt ctgcttgtgc aacctgcgac     420
ggtttcttct atcgcaacca gaaagttgcg gtcatcggcg gcggcaatac cgcggttgaa     480
gaggcgctgt atctgtctaa catcgcttcg gaagtgcatc tgattcaccg ccgtgacggt     540
ttccgcgcgg aaaaaatcct cattaagcgc ctgatggata agtggagaa cggcaacatc     600 attctgcaca ccaaccgtac gctggaagaa gtgaccggcg atcaaatggg tgtcactggc     660
gttcgtctgc gcgatacgca aacagcgat aacatcgagt cactcgacgt tgccggtctg     720
tttgttgcta tcggtcacag cccgaatact gcgattttcg aagggcagct ggaactggaa     780
aacggctaca tcaaagtaca gtcgggtatt catggtaatg ccacccagac cagcattcct     840
ggcgtctttg ccgcaggcga cgtgatggat cacatttatc gccaggccat tacttcggcc     900
ggtacaggct gcatggcagc acttgatgcg gaacgctacc tcgatggttt agctgacgca     960
aaataa                                                               966

<210> SEQ ID NO 10
<211> LENGTH: 321
<212> TYPE: PRT
<213> ORGANISM: Escherichia coli

<400> SEQUENCE: 10

Met Gly Thr Thr Lys His Ser Lys Leu Leu Ile Leu Gly Ser Gly Pro
1               5                   10                  15

Ala Gly Tyr Thr Ala Ala Val Tyr Ala Ala Arg Ala Asn Leu Gln Pro
            20                  25                  30

Val Leu Ile Thr Gly Met Glu Lys Gly Gly Gln Leu Thr Thr Thr Thr
        35                  40                  45

Glu Val Glu Asn Trp Pro Gly Asp Pro Asn Asp Leu Thr Gly Pro Leu
    50                  55                  60

Leu Met Glu Arg Met His Glu His Ala Thr Lys Phe Glu Thr Glu Ile
65                  70                  75                  80

Ile Phe Asp His Ile Asn Lys Val Asp Leu Gln Asn Arg Pro Phe Arg
                85                  90                  95

Leu Asn Gly Asp Asn Gly Glu Tyr Thr Cys Asp Ala Leu Ile Ile Ala
            100                 105                 110

Thr Gly Ala Ser Ala Arg Tyr Leu Gly Leu Pro Ser Glu Glu Ala Phe
        115                 120                 125

Lys Gly Arg Gly Val Ser Ala Cys Ala Thr Cys Asp Gly Phe Phe Tyr
    130                 135                 140

Arg Asn Gln Lys Val Ala Val Ile Gly Gly Gly Asn Thr Ala Val Glu
145                 150                 155                 160

Glu Ala Leu Tyr Leu Ser Asn Ile Ala Ser Glu Val His Leu Ile His
```

```
                  165                 170                 175
Arg Arg Asp Gly Phe Arg Ala Glu Lys Ile Leu Ile Lys Arg Leu Met
            180                 185                 190

Asp Lys Val Glu Asn Gly Asn Ile Ile Leu His Thr Asn Arg Thr Leu
            195                 200                 205

Glu Glu Val Thr Gly Asp Gln Met Gly Val Thr Gly Val Arg Leu Arg
            210                 215                 220

Asp Thr Gln Asn Ser Asp Asn Ile Glu Ser Leu Asp Val Ala Gly Leu
225                 230                 235                 240

Phe Val Ala Ile Gly His Ser Pro Asn Thr Ala Ile Phe Glu Gly Gln
                245                 250                 255

Leu Glu Leu Glu Asn Gly Tyr Ile Lys Val Gln Ser Gly Ile His Gly
            260                 265                 270

Asn Ala Thr Gln Thr Ser Ile Pro Gly Val Phe Ala Ala Gly Asp Val
            275                 280                 285

Met Asp His Ile Tyr Arg Gln Ala Ile Thr Ser Ala Gly Thr Gly Cys
            290                 295                 300

Met Ala Ala Leu Asp Ala Glu Arg Tyr Leu Asp Gly Leu Ala Asp Ala
305                 310                 315                 320

Lys

<210> SEQ ID NO 11
<211> LENGTH: 1353
<212> TYPE: DNA
<213> ORGANISM: Escherichia coli

<400> SEQUENCE: 11
atgactaaac actatgatta catcgccatc ggcggcggca gcggcggtat cgcctccatc     60
aaccgcgcgg ctatgtacgg ccagaaatgt gcgctgattg aagccaaaga gctgggcggc    120
acctgcgtaa atgttggctg tgtgccgaaa aaagtgatgt ggcacgcggc gcaaatccgt    180
gaagcgatcc atatgtacgg cccggattat ggttttgata ccactatcaa taaattcaac    240
tgggaaacgt tgatcgccag ccgtaccgcc tatatcgacc gtattcatac ttcctatgaa    300
aacgtgctcg gtaaaaataa cgttgatgta atcaaaggct tgcccgctt cgttgatgcc    360 aaaacgctgg aggtaaacgg cgaaaccatc acggccgatc atattctgat cgccacaggc    420
ggtcgtccga gccaccccgga tattccgggc gtggaatacg gtattgattc tgatggcttc    480
ttcgcccttc ctgctttgcc agagcgcgtg gcggttgttg gcgcgggtta catcgccgtt    540
gagctggcgg gcgtgattaa cggcctcggc gcgaaaacgc atctgtttgt gcgtaaacat    600
gcgccgctgc gcagcttcga cccgatgatt tccgaaacgc tggtcgaagt gatgaacgcc    660
gaaggcccgc agctgcacac caacgccatc ccgaaagcgg tagtgaaaaa taccgatggt    720
agcctgacgc tggagctgga agatggtcgc agtgaaacgg tggattgcct gatttgggcg    780
attggtcgcg agcctgccaa tgacaacatc aacctggaag ccgctggcgt aaaactaac     840 gaaaaaggct atatcgtcgt cgataaatat caaaacacca atattgaagg tatttacgcg    900
gtgggcgata acacgggtgc agtggagctg acaccggtgg cagttgcagc gggtcgccgt    960
ctctctgaac gcctgtttaa taacaagccg atgagcatc tggattacag caacattccg   1020
accgtggtct tcagccatcc gccgattggt actgttggtt aacggaaacc gcaggcgcgc   1080
gagcagtatg cgacgatca ggtgaaagtg tataaatcct ctttcaccgc gatgtatacc   1140
gccgtcacca ctcaccgcca gccgtgccgc atgaagctgg tgtgcgttgg atcggaagag   1200
```

-continued

```
aagattgtcg gtattcacgg cattggcttt ggtatggacg aaatgttgca gggcttcgcg    1260
gtggcgctga agatgggggc aaccaaaaaa gacttcgaca ataccgtcgc cattcaccca    1320
acggcggcag aagagttcgt gacaatgcgt taa                                 1353
```

<210> SEQ ID NO 12
<211> LENGTH: 450
<212> TYPE: PRT
<213> ORGANISM: Escherichia coli

<400> SEQUENCE: 12

```
Met Thr Lys His Tyr Asp Tyr Ile Ala Ile Gly Gly Ser Gly Gly
1               5                   10                  15

Ile Ala Ser Ile Asn Arg Ala Ala Met Tyr Gly Gln Lys Cys Ala Leu
                20                  25                  30

Ile Glu Ala Lys Glu Leu Gly Gly Thr Cys Val Asn Val Gly Cys Val
                35                  40                  45

Pro Lys Lys Val Met Trp His Ala Ala Gln Ile Arg Glu Ala Ile His
    50                  55                  60

Met Tyr Gly Pro Asp Tyr Gly Phe Asp Thr Thr Ile Asn Lys Phe Asn
65                  70                  75                  80

Trp Glu Thr Leu Ile Ala Ser Arg Thr Ala Tyr Ile Asp Arg Ile His
                85                  90                  95

Thr Ser Tyr Glu Asn Val Leu Gly Lys Asn Asn Val Asp Val Ile Lys
                100                 105                 110

Gly Phe Ala Arg Phe Val Asp Ala Lys Thr Leu Glu Val Asn Gly Glu
            115                 120                 125

Thr Ile Thr Ala Asp His Ile Leu Ile Ala Thr Gly Gly Arg Pro Ser
    130                 135                 140

His Pro Asp Ile Pro Gly Val Glu Tyr Gly Ile Asp Ser Asp Gly Phe
145                 150                 155                 160

Phe Ala Leu Pro Ala Leu Pro Glu Arg Val Ala Val Val Gly Ala Gly
                165                 170                 175

Tyr Ile Ala Val Glu Leu Ala Gly Val Ile Asn Gly Leu Gly Ala Lys
                180                 185                 190

Thr His Leu Phe Val Arg Lys His Ala Pro Leu Arg Ser Phe Asp Pro
            195                 200                 205

Met Ile Ser Glu Thr Leu Val Glu Val Met Asn Ala Glu Gly Pro Gln
    210                 215                 220

Leu His Thr Asn Ala Ile Pro Lys Ala Val Val Lys Asn Thr Asp Gly
225                 230                 235                 240

Ser Leu Thr Leu Glu Leu Glu Asp Gly Arg Ser Glu Thr Val Asp Cys
                245                 250                 255

Leu Ile Trp Ala Ile Gly Arg Glu Pro Ala Asn Asp Asn Ile Asn Leu
                260                 265                 270

Glu Ala Ala Gly Val Lys Thr Asn Glu Lys Gly Tyr Ile Val Val Asp
            275                 280                 285

Lys Tyr Gln Asn Thr Asn Ile Glu Gly Ile Tyr Ala Val Gly Asp Asn
    290                 295                 300

Thr Gly Ala Val Glu Leu Thr Pro Val Ala Val Ala Ala Gly Arg Arg
305                 310                 315                 320

Leu Ser Glu Arg Leu Phe Asn Asn Lys Pro Asp Glu His Leu Asp Tyr
                325                 330                 335

Ser Asn Ile Pro Thr Val Val Phe Ser His Pro Pro Ile Gly Thr Val
                340                 345                 350
```

```
Gly Leu Thr Glu Pro Gln Ala Arg Glu Gln Tyr Gly Asp Asp Gln Val
        355                 360                 365

Lys Val Tyr Lys Ser Ser Phe Thr Ala Met Tyr Thr Ala Val Thr Thr
    370                 375                 380

His Arg Gln Pro Cys Arg Met Lys Leu Val Cys Val Gly Ser Glu Glu
385                 390                 395                 400

Lys Ile Val Gly Ile His Gly Ile Gly Phe Gly Met Asp Glu Met Leu
                405                 410                 415

Gln Gly Phe Ala Val Ala Leu Lys Met Gly Ala Thr Lys Lys Asp Phe
            420                 425                 430

Asp Asn Thr Val Ala Ile His Pro Thr Ala Ala Glu Glu Phe Val Thr
                435                 440                 445

Met Arg
    450

<210> SEQ ID NO 13
<211> LENGTH: 1557
<212> TYPE: DNA
<213> ORGANISM: Escherichia coli

<400> SEQUENCE: 13
```

| | | | | | |
|---|---|---|---|---|---|
| ttgatcccgg | acgtatcaca | ggcgctggcc | tggctggaaa | acatcctca | ggcgttaaag | 60 |
| gggatacagc | gtgggctgga | gcgcgaaact | ttgcgtgtta | tgctgatgg | cacactggca | 120 |
| acaacaggtc | atcctgaagc | attaggttcc | gcactgacgc | acaaatggat | tactaccgat | 180 |
| tttgcggaag | cattgctgga | attcattaca | ccagtggatg | gtgatattga | acatatgctg | 240 |
| acctttatgc | gcgatctgca | tcgttatacg | gcgcgcaata | tgggcgatga | gcggatgtgg | 300 |
| ccgttaagta | tgccatgcta | catcgcagaa | ggtcaggaca | tcgaactggc | acagtacggc | 360 |
| acttctaaca | ccggacgctt | taaaacgctg | tatcgtgaag | ggctgaaaaa | tcgctacggc | 420 |
| gcgctgatgc | aaaccatttc | cggcgtgcac | tacaatttct | ctttgccaat | ggcattctgg | 480 |
| caagcgaagt | gcggtgatat | ctcgggcgct | gatgccaaag | agaaaatttc | tgcgggctat | 540 |
| ttccgcgtta | tccgcaatta | ctatcgtttc | ggttgggtca | ttccttatct | gtttggtgca | 600 |
| tctccggcga | tttgttcttc | tttcctgcaa | ggaaaaccaa | cgtcgctgcc | gtttgagaaa | 660 |
| accgagtgcg | gtatgtatta | cctgccgtat | gcgacctctc | ttcgtttgag | cgatctcggc | 720 |
| tataccaata | aatcgcaaag | caatcttggt | attaccttca | acgatcttta | cgagtacgta | 780 |
| gcgggcctta | acaggcaat | caaaacgcca | tcggaagagt | acgcgaagat | tggtattgag | 840 |
| aaagacggta | agaggctgca | aatcaacagc | aacgtgttgc | agattgaaaa | cgaactgtac | 900 |
| gcgccgattc | gtccaaaacg | cgttaccgc | agcggcgagt | cgccttctga | tgcgctgtta | 960 |
| cgtggcggca | ttgaatatat | tgaagtgcgt | tcgctggaca | tcaacccgtt | ctcgccgatt | 1020 |
| ggtgtagatg | aacagcaggt | gcgattcctc | gacctgttta | tggtctggtg | tgcgctggct | 1080 |
| gatgcaccgg | aaatgagcag | tagcgaactt | gcctgtacac | gcgttaactg | gaaccgggtg | 1140 |
| atcctcgaag | gtcgcaaacc | gggtctgacg | ctgggtatcg | gctgcgaaac | cgcacagttc | 1200 |
| ccgttaccgc | aggtgggtaa | agatctgttc | cgcgatctga | aacgcgtcgc | gcaaacgctg | 1260 |
| gatagtatta | acggcggcga | agcgtatcag | aaagtgtgtg | atgaactggt | tgcctgcttc | 1320 |
| gataatcccg | atctgacttt | ctctgcccgt | atcttaaggt | ctatgattga | tactggtatt | 1380 |
| ggcggaacag | gcaaagcatt | tgcagaagcc | taccgtaatc | tgctgcgtga | agagccgctg | 1440 |
| gaaattctgc | gcgaagagga | ttttgtagcc | gagcgcgagg | cgtctgaacg | ccgtcagcag | 1500 | gaaatggaag ccgctgatac cgaaccgttt gcggtgtggc tggaaaaaca cgcctga    1557

<210> SEQ ID NO 14
<211> LENGTH: 518
<212> TYPE: PRT
<213> ORGANISM: Escherichia coli

<400> SEQUENCE: 14

Met Ile Pro Asp Val Ser Gln Ala Leu Ala Trp Leu Glu Lys His Pro
1               5                   10                  15

Gln Ala Leu Lys Gly Ile Gln Arg Gly Leu Glu Arg Glu Thr Leu Arg
            20                  25                  30

Val Asn Ala Asp Gly Thr Leu Ala Thr Thr Gly His Pro Glu Ala Leu
        35                  40                  45

Gly Ser Ala Leu Thr His Lys Trp Ile Thr Thr Asp Phe Ala Glu Ala
    50                  55                  60

Leu Leu Glu Phe Ile Thr Pro Val Asp Gly Asp Ile Glu His Met Leu
65                  70                  75                  80

Thr Phe Met Arg Asp Leu His Arg Tyr Thr Ala Arg Asn Met Gly Asp
                85                  90                  95

Glu Arg Met Trp Pro Leu Ser Met Pro Cys Tyr Ile Ala Glu Gly Gln
            100                 105                 110

Asp Ile Glu Leu Ala Gln Tyr Gly Thr Ser Asn Thr Gly Arg Phe Lys
        115                 120                 125

Thr Leu Tyr Arg Glu Gly Leu Lys Asn Arg Tyr Gly Ala Leu Met Gln
    130                 135                 140

Thr Ile Ser Gly Val His Tyr Asn Phe Ser Leu Pro Met Ala Phe Trp
145                 150                 155                 160

Gln Ala Lys Cys Gly Asp Ile Ser Gly Ala Asp Ala Lys Glu Lys Ile
                165                 170                 175

Ser Ala Gly Tyr Phe Arg Val Ile Arg Asn Tyr Tyr Arg Phe Gly Trp
            180                 185                 190

Val Ile Pro Tyr Leu Phe Gly Ala Ser Pro Ala Ile Cys Ser Ser Phe
        195                 200                 205

Leu Gln Gly Lys Pro Thr Ser Leu Pro Phe Glu Lys Thr Glu Cys Gly
    210                 215                 220

Met Tyr Tyr Leu Pro Tyr Ala Thr Ser Leu Arg Leu Ser Asp Leu Gly
225                 230                 235                 240

Tyr Thr Asn Lys Ser Gln Ser Asn Leu Gly Ile Thr Phe Asn Asp Leu
                245                 250                 255

Tyr Glu Tyr Val Ala Gly Leu Lys Gln Ala Ile Lys Thr Pro Ser Glu
            260                 265                 270

Glu Tyr Ala Lys Ile Gly Ile Glu Lys Asp Gly Lys Arg Leu Gln Ile
        275                 280                 285

Asn Ser Asn Val Leu Gln Ile Glu Asn Glu Leu Tyr Ala Pro Ile Arg
    290                 295                 300

Pro Lys Arg Val Thr Arg Ser Gly Glu Ser Pro Ser Asp Ala Leu Leu
305                 310                 315                 320

Arg Gly Gly Ile Glu Tyr Ile Glu Val Arg Ser Leu Asp Ile Asn Pro
                325                 330                 335

Phe Ser Pro Ile Gly Val Asp Glu Gln Gln Val Arg Phe Leu Asp Leu
            340                 345                 350

```
Phe Met Val Trp Cys Ala Leu Ala Asp Ala Pro Glu Met Ser Ser Ser
        355                 360                 365

Glu Leu Ala Cys Thr Arg Val Asn Trp Asn Arg Val Ile Leu Glu Gly
    370                 375                 380

Arg Lys Pro Gly Leu Thr Leu Gly Ile Gly Cys Glu Thr Ala Gln Phe
385                 390                 395                 400

Pro Leu Pro Gln Val Gly Lys Asp Leu Phe Arg Asp Leu Lys Arg Val
                405                 410                 415

Ala Gln Thr Leu Asp Ser Ile Asn Gly Gly Glu Ala Tyr Gln Lys Val
                420                 425                 430

Cys Asp Glu Leu Val Ala Cys Phe Asp Asn Pro Asp Leu Thr Phe Ser
                435                 440                 445

Ala Arg Ile Leu Arg Ser Met Ile Asp Thr Gly Ile Gly Gly Thr Gly
                450                 455                 460

Lys Ala Phe Ala Glu Ala Tyr Arg Asn Leu Leu Arg Glu Glu Pro Leu
465                 470                 475                 480

Glu Ile Leu Arg Glu Glu Asp Phe Val Ala Glu Arg Glu Ala Ser Glu
                485                 490                 495

Arg Arg Gln Gln Glu Met Glu Ala Ala Asp Thr Glu Pro Phe Ala Val
                500                 505                 510

Trp Leu Glu Lys His Ala
        515

<210> SEQ ID NO 15
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Ala Leu Val Ile Tyr
        35                  40                  45

Tyr Gly Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Trp
                85                  90                  95

Val Phe Gly Gly Gly Thr Lys Leu Thr Val Leu
                100                 105
```